United States Patent
Hafenbradl et al.

(10) Patent No.: US 11,873,534 B2
(45) Date of Patent: Jan. 16, 2024

(54) METHOD FOR CONTROLLING THE QUALITY

(71) Applicant: Electrochaea GmbH, Planegg (DE)

(72) Inventors: Doris Hafenbradl, Pullach (DE); Felix Popp, Munich (DE)

(73) Assignee: Electrochaea GmbH, Planegg (DE)

( * ) Notice: Subject to any disclaimer, the term of this patent is extended or adjusted under 35 U.S.C. 154(b) by 0 days.

(21) Appl. No.: 17/757,341

(22) PCT Filed: Dec. 11, 2020

(86) PCT No.: PCT/EP2020/085817
§ 371 (c)(1),
(2) Date: Jun. 14, 2022

(87) PCT Pub. No.: WO2021/122389
PCT Pub. Date: Jun. 24, 2021

(65) Prior Publication Data
US 2023/0035903 A1    Feb. 2, 2023

(30) Foreign Application Priority Data

Dec. 16, 2019  (DE) .......................... 102019134589.9
Jan. 22, 2020  (DE) .......................... 102019101487.2

(51) Int. Cl.
*C12Q 1/689*    (2018.01)
*C12Q 1/6844*   (2018.01)
*C12Q 1/6869*   (2018.01)

(52) U.S. Cl.
CPC .......... *C12Q 1/689* (2013.01); *C12Q 1/6844* (2013.01); *C12Q 1/6869* (2013.01); *C12Q 2600/156* (2013.01)

(58) Field of Classification Search
CPC .......................... C12Q 1/689; C12Q 2600/156
See application file for complete search history.

(56) References Cited

U.S. PATENT DOCUMENTS 8,603,748 B2    12/2013    Fratamico et al.

FOREIGN PATENT DOCUMENTS

| DE | 102020101487 B2 | 2/2022 |
| DE | 102020101487 B4 | 2/2022 |
| WO | 2021122389 A1 | 6/2021 |

OTHER PUBLICATIONS

Elliott et al., Multiplex T-RFLP Allows for Increased Target Number and Specificity: Detection of *Salmonella enterica* and Six Species of *Listeria* in a Single Test, PLOS One (Aug. 24, 2012), 7(8): e43672. doi:10.1371/journal.pone.0043672.
German Office Action dated Jun. 29, 2021 for German Patent Application No. DE102020101487-2, with English translation.
Decision to Grant a Patent dated Nov. 16, 2021, for German Patent Application No. DE102020101487-2, with English Translation.
International Search Report and Written Opinion for International PCT Application No. PCT/EP2020/085817, dated Mar. 31, 2021.

(Continued)

*Primary Examiner* — Diana B Johannsen
(74) *Attorney, Agent, or Firm* — K&L Gates LLP

(57) ABSTRACT

The present invention refers to a method for typing Archaea and quickly discriminating contaminants in pure strain cultures of methanogenic Archaea, leading to isolation of variants with mutations from the culture population.

Figure 1:
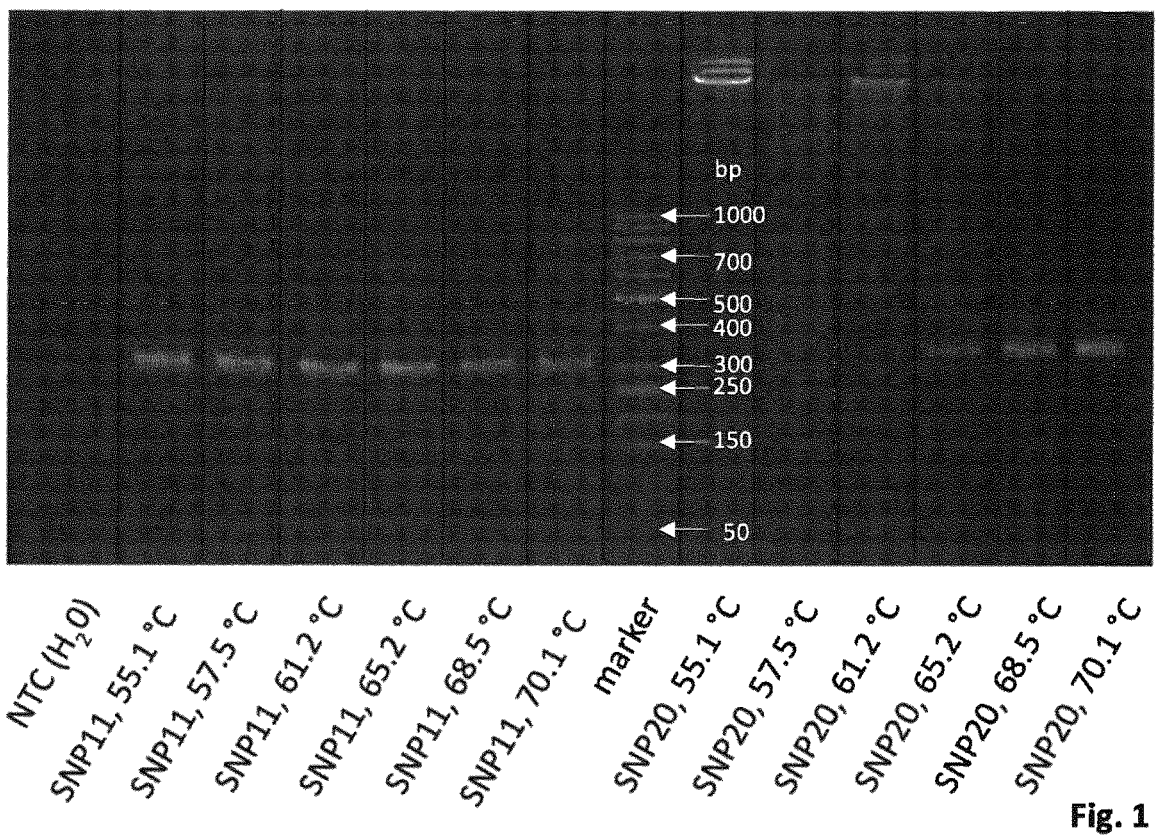

16 Claims, 9 Drawing Sheets
Specification includes a Sequence Listing.

(56) References Cited

OTHER PUBLICATIONS

Cleland et al., Use of the DiversiLab repetitive sequence-based PCR system for genotyping and identification of Archaea, Journal of Microbiological Methods (May 1, 2008), 72(2):172-178—Abstract only.
Sawayama et al., Phylogenetic description of immobilized methanogenic community using real-time PCR in a fixed-bed anaerobic digester, Bioresource Technology (Jan. 1, 2006), 97(1):69-76—Abstract only.
Lee et al., Group-specific primer and probe sets to detect methanogenic communities using quantitative real-time polymerase chain reaction, Biotechnology and Bioengineering (Mar. 1, 2005), 89(6):670-679—Abstract only.

SEQUENCE LISTING

<160> NUMBER OF SEQ ID NOS: 6

<210> SEQ ID NO 1
<211> LENGTH: 21
<212> TYPE: DNA
<213> ORGANISM: Methanothermobacter thermautotrophicus
<220> FEATURE:
<223> OTHER INFORMATION: primer forward

<400> SEQUENCE: 1
tcggcccagt atttctcatg g                                              21

<210> SEQ ID NO 2
<211> LENGTH: 20
<212> TYPE: DNA
<213> ORGANISM: Methanothermobacter thermautotrophicus
<220> FEATURE:
<223> OTHER INFORMATION: Primer forward

<400> SEQUENCE: 2
tgggtcacgt gttcgatgac                                                20

<210> SEQ ID NO 3
<211> LENGTH: 20
<212> TYPE: DNA
<213> ORGANISM: Methanothermobacter thermautotrophicus
<220> FEATURE:
<223> OTHER INFORMATION: Primer forward

<400> SEQUENCE: 3
ctccacaaag acgtcctccc                                                20

<210> SEQ ID NO 4
<211> LENGTH: 20
<212> TYPE: DNA
<213> ORGANISM: Methanothermobacter thermautotrophicus
<220> FEATURE:
<223> OTHER INFORMATION: Primer reverse

<400> SEQUENCE: 4
tgggtggaat gggtggaatg                                                20

<210> SEQ ID NO 5
<211> LENGTH: 20
<212> TYPE: DNA
<213> ORGANISM: Methanothermobacter thermautotrophicus
<220> FEATURE:
<223> OTHER INFORMATION: Primer reverse

<400> SEQUENCE: 5
tatgaactcc acgaggtgcc                                                20

<210> SEQ ID NO 6
<211> LENGTH: 21
<212> TYPE: DNA

```
<213> ORGANISM: Methanothermobacter thermautotrophicus
<220> FEATURE:
<223> OTHER INFORMATION: Primer reverse

<400> SEQUENCE: 6
tttagttgga ggaggatggg g                                              21
```

METHOD FOR CONTROLLING THE QUALITY

CROSS-REFERENCE TO RELATED APPLICATIONS

This application is a U.S. National Stage Entry under 35 U.S.C. § 371 of International Patent Application No. PCT/EP2020/085817, entitled METHOD FOR CONTROLLING THE QUALITY, filed Dec. 11, 2020, which claims the benefit of German Patent Application No. 102019134589.9, filed Dec. 16, 2019 and German Patent Application No. 102020101487.2, filed Jan. 22, 2020, the entire disclosures of which are hereby incorporated by reference herein.

The present invention refers to a method for typing Archaea and quickly discriminating contaminants in pure strain cultures of methanogenic Archaea.

The pursuit of efficient energy supplying solutions at a lower cost for the environment is a challenge set forth by climate action programs all over the world, from the European Commission, the US groups of businesses and environmental and governmental associations, Japan in its attempt to replace nuclear energy for electricity supply in the aftermath of the tragic incident of Fukushima, to the seven emerging economies and, thus, an endeavor globally undertaken by member countries to counteract climate changes and eventually stabilize the temperature of the planet. The ultimate goal is to fulfill the increasing need for sustainable and renewable energy while counteracting climate change towards the transition to a low carbon modern economy.

Methane has the highest energy density per carbon atom among volatile hydrocarbons and its potential for energy conversion is far greater than any other natural gas, obtained directly by combustion in presence of oxygen or using fuel cells to produce electricity.

As natural gas, therefore, methane constitutes a sustainable and renewable energy source and already today increasingly substitutes coal and other fossil fuels. However, the side quests of a dramatic reduction of the environmental impact and viability of its production, storage and transportation are not yet completed.

One of the main technical disadvantages in the exploitation of methane on a large scale is related to e.g. the high level of contaminants remaining in fossil natural gas, and therefore a need for costly purification procedures. Furthermore, a long list of still unsolved issues such as a necessity for adequate storage plants for methane, the related needs for better pressurized containment systems, odour from amassing of large quantities of gas, mostly from sulphate-rich contaminants in the natural gas, the risk of explosions, leakages during transportation and storage, all these presently hamper and delay the exploitation of methane.

Nevertheless, methane's potential for energy generation has become increasingly relevant in the global market. Recent research has therefore focused on the development and improvement of methods for producing methane with methanogens, e.g. Archaea, which are capable of producing renewable methane from carbon dioxide and hydrogen very efficiently. Presently, the state of the art describes several attempts to enrich gas compositions with methane produced by employing methanogenic microorganisms. For industrial production of methane using Archaea, e.g., *Methanothermobacter thermoautotrophicus* strain DSM3590—deposited and commercially available from DSMZ, the German collection of microorganism and cell culture—is regularly used.

This type of methane production happens in suitable bioreactors/cells and may be easily set up all over the world, in any setting poor of infrastructures, requiring raw materials generally present in the atmosphere. Most importantly, it generally yields gas compositions enriched with methane and a lower amount of contaminants, wherein such compositions are expected to require less effort until ready to be fed into energy supplying systems. Moreover, its conversion into energy, dealing only carbon dioxide and water, is the cleanest among hydrocarbon fuels.

Upgrading biomethane production to an established scalable and reliable renewable energy source proves to remain a challenge, especially owing to the requirement for a continuous process.

Nevertheless, because of its promising potential, the large-scale utilization of biomethane is under attentive political and economic scrutiny, to render the technology remunerative and cost-effective, and harnessing methane has been identified as the most important near-term goal for biochemical engineering. Therefore, effective solutions to the above disadvantages and improvements of production processes driven by methanogenic Archaea are urgently needed.

One important component in the enablement of efficient production of methane enriched gas compositions are distinct strains of methanogenic microorganisms, which are characterized by and demonstrate an uniform behavior in response to a number of parameters. It is supported by evidence that efficient methanation is linked to this uniformity of behavior and thus to the purity of said culture.

Like normal heterogeneous cultures, also culture that start from a pure strain may undergo adaptation during their life cycles, for example owing to transitional parameters fluctuation, resulting in the appearance of modified organisms in the culture. While the adaptation of a natural system may usually be ascribed to natural coping mechanisms and it is intended to improve the culture and make the best fruition of the resources available in the surrounding environment, in the long term the appearance of genetically modified organisms by adaptation processes may cause a global system alteration.

Existing methods for accurately typing of Archaea, either using fatty acids analysis (Darla V. Dibrova, Environ Microbiol. 2014 April; 16(4): 907-918; Villanueva L. et al., Environ Microbiol. 2017 January; 19(1):54-69. doi: 10.1111/1462-2920.13361. Epub 2016 Jul. 7), riboprinting (Clark C G, J Eukaryot Microbiol. 1997 July-August; 44(4): 277-83), phenotyping or PCR techniques are, respectively, not precise, not accurate and not widely accessible and/or directly available. Moreover, they only help discriminating among genera or families of microorganisms but not among species. Further, their ability to provide high-resolution results for a pure strain culture in conditions of fluctuating parameters have neither being suggested nor tested in these documents.

Moreover, strategies for identifying methanogenic Archaea in soil, feces, cultures or other similar substrates or ecological niches are fairly recent, some dating back less than a decade, and may be ascribed, among other reasons, to the rising interest for differentiating among microorganisms capable of carbon dioxide sequestration in said substrates for the purpose of producing enhanced biofuel. Moreover, the difficulty to separate between species in case of colonies of microorganisms in complex environments, because of synergic behaviors of said species may deliver and perpetuate inaccuracies, to the point that already just discriminating among different species from available clone libraries may reveal a daunting task.

In particular, Cleland et al., 2008 have tested a repetitive sequenced-based PCR method, mostly developed for bacteria and used for source tracking of hospital and community infection, contamination and epidemiological surveillance, for genotyping and identification of Archaea. In their paper, they focused on methanogens and extreme halophiles, in cultures wherein growth phase and growth content had not been systematically varied. It is well known how the fluctuations of these parameters may induce structural DNA alterations, rendering questionable the reliability of any such results in the application to pure cultures undergoing constant variations in their feeding supply and microenvironment, and wherein the maintenance of said purity is paramount to the provision of an efficient methanation process.

Their method employs the PCR amplification of intervening repetitive short DNA stretches to the discrimination of different species of Archaea; nevertheless, although it shows effectiveness, it has not been reported to work in variable environment and with a low variability culture, in terms of its components.

Expectations of heterogeneity in uncontrolled/natural environments certainly prompt methods for coarse identification and/or discrimination and/or isolation of different species but may not offer a targeted high-resolution assaying method for pure cultures in controlled environments, wherein the expectation of heterogeneity is lower.

Mutation within the same species may occur owing to adaptation to culture conditions and the microenvironment across the culture.

In this framework, the discrimination and/or isolation of differences within the same species, brought along by adaptation and resulting in very small variations would require an extremely accurate methodology to identify these small variations by targeting them exactly, but without of course knowing beforehand where such small variations can be found.

There is therefore a need for providing rapid and inexpensive quality ensuring assays of a monoculture utilizing pure strains, and further methods, specific enough to also allow discriminating between variations within the same species.

It is thus an object of the present invention to overcome the described disadvantages of the state of the art, especially to provide a reliable, quick and effective method for typing Archaea to ensure pure culture strains. Thereby, it is thus a further object of the present invention to establish a fast and efficient test for pure Archaea strain cultures during their normal life cycle, which can be even optimized by a parallel reciprocal test approach to enable quality control and genotyping in dynamic environments.

In the current trend of technological improvement to stabilize and potentiate the methane production processes employing variable gas compositions while still guaranteeing an effluent methane gas composition of high purity, accurate quality control of culture composition plays an important role.

Within this framework of technical advancements, the present invention therefore provides, as explicitly specified in the claims, teachings on how to effectively test for the presence of pure methanogenic microorganism *Methanothermobacter thermoautotrophicus* DSM3590 (in the following *M. thermoautotrophicus* DSM3590 or M. t. DSM3590) and to distinguish it from other Archaea. Further, it is taught how to test for the quality and purity of a given composition of an Archaea strain culture involved in the continuous methanogenic process as well as effectively genotyping variants in said culture.

The object of the present application has been solved by the newly developed method as specified in claim 2 of the present invention utilizing PCR primer pairs as specified in claim 1 of the present invention. Further embodiments refer to variations of this newly developed method as well as a quality control kit for use in detecting the presence of methanogenic microorganism *Methanothermobacter thermoautotrophicus* DSM3590 within a given sample. Additionally, the method provides for the identification of *M. thermoautotrophicus* DSM3590 variants identified by said kit and isolated as described in the subsequent dependent claims.

In particular, to achieve the stated goal, the present invention provides a first polymerase chain reaction (PCR) primer selected from the nucleotide sequence SEQ ID NO:1; SEQ ID NO:2 or SEQ ID NO:3 and/or a second polymerase chain reaction primer selected from the nucleotide sequence SEQ ID NO:4; SEQ ID NO:5 or SEQ ID NO:6, wherein each of the first and each of the second primers are capable to hybridize with the DNA of the methanogenic microorganism *M. thermoautotrophicus* DSM3590 and wherein SEQ ID NO:1 and SEQ ID NO:4; as well as SEQ ID NO:2 and SEQ ID NO:5; as well as SEQ ID NO:3 and SEQ ID NO:6 build up a primer pair to be used for PCR amplification of parts of a genomic DNA sequence of *M. thermoautotrophicus* DSM3590.

The strain "*Methanothermobacter thermoautotrophicus*, DSM3590" used in the present application is also known as *M. thermoautotrophicus* str. hveragerdi and is commercially available at the DSMZ, German collection of Microorganisms and cell cultures. Interestingly, it must be understood that no sequence data is available for this strain.

The inventors of the present invention have set themselves the task to provide a simplified method for the identification of *M. thermoautotrophicus* DSM3590 in a given sample comprising Archaea in comparison with time consuming state of the art methods, e.g. genome sequencing and/or amplicon sequencing.

In the beginning the inventors designed various random primers with the purpose that these are suitable to amplify DNA sequences of *M. thermoautotrophicus* DSM3590 and to be suitable to distinguish DNA sequences of *M. thermoautotrophicus* DSM3590 from DNA sequences of other non-M.-t.-DSM3590 Archaea by test and error experimentation.

In other words, the inventors of the present invention developed primer pairs to specifically amplify gene sequences of the species *M. thermoautotrophicus*, DSM3590 and as ruled out by test and error experimentation are not suitable to PCR amplify gene sequences of Archaea species other than *M. thermoautotrophicus*, DSM3590, thus allowing for differentiation towards these other Archaea species. Thus, the idea was the use of these primers in a PCR reaction allows for testing if in a sample comprising Archaea DNA *M. thermoautotrophicus*, DSM3590 DNA is present and exclusively present.

Surprisingly, the inventors found that out of the multitude of tested primers the disclosed primers according to the present invention not only amplify DNA sequences of *M. thermoautotrophicus* DSM3590 but were suitable to also amplify DNA sequences of at least one other non-*Methanothermobacter thermoautotrophicus* Archaea.

Even more interestingly the inventors found that the amplicons generated by the primers of the present invention comprised single nucleotide variations within the primer amplified DNA sequences (amplicons) compared to other non-*Methanothermobacter-thermoautotrophicus* Archaea, and also compared to other *M. thermoautotrophicus* DSM3590 related variants. These single nucleotide variations were found to allow for differentiation of *M. thermoautotrophicus* DSM3590 towards other non-M.-t.-DSM3590 Archaea and even towards other *M. thermoautotrophicus* DSM3590 related variants using specific downstream digestion reactions as specified herein in the following.

Thus, the particularly surprising effect, which renders the primers according to the present invention different from other ordinary primers able to bind to nucleic acid sequences of methanogenic microorganisms relies in their ability to discriminate with high resolution within the same species, enabling the identification of variations of sequences that with other primers would have been attributed to the same identical species from which the variation has emerged.

Said PCR primer pairs are used in the method for detecting the presence of methanogenic microorganism *M. thermoautotrophicus* DSM3590 according to the present invention, comprising the steps of:
  obtaining a sample containing methanogenic microorganisms (cells) and applying means and techniques to release the DNA from the microorganisms to receive an unpurified DNA sample or obtaining a sample containing purified DNA of the methanogenic microorganisms;
  using the unpurified DNA sample or the purified DNA sample according to step a. in a PCR amplification using a primer pair comprising a first and a second primer according to claim 1, to receive an amplified DNA sequence (amplicon), wherein the amplicon comprises at least one restriction enzyme recognition sequence;
  purifying the respective amplicon;
  performing a first digestion reaction with the amplicon of step c. by incubating the amplicon in a reaction buffer with at least one first restriction enzyme, which recognizes a first recognition sequence for a time sufficient to form restriction fragments;
  determining the number of the formed restriction fragments and their size (restriction pattern), e.g. via gel electrophoresis; and
  genotyping the methanogenic microorganism on the basis of the restriction pattern;
  optionally, sequencing the purified amplicon of step c. or at least parts thereof and/or the amplicon following the digestion reaction of step d. or at least parts thereof.

To test whether the inventive primer pairs specifically amplified *M. thermoautotrophicus*, DSM3590 the inventors subsequent to the PCR amplification performed a quality control by exposing the amplicon generated using said primers of the present invention in a digestion reaction by applying a first restriction enzyme. Interestingly, the first restriction enzyme recognizing a first recognition sequence, was not digesting the amplicon of *M. thermoautotrophicus* DSM3590.

However, surprisingly, the inventors of the present invention by performing said restriction enzyme digestion reactions with the specific amplicons using a sample supposedly comprising only Archaea species of *M. thermoautotrophicus* DSM3590 (i.e. the sample was assumed to be a pure monoculture strain sample) identified a restriction pattern unrelated to that of *M. thermoautotrophicus* DSM3590. This unrelated restriction pattern indicated the presence of a strain variant of DSM3590, i.e. the inventors found that more than the expected one restriction fragment was visible using gel electrophoresis analysis.

By further testing including amplicon sequencing the inventors found out that said primers were also capable to amplify DNA sequence of other *M. thermoautotrophicus* strains different from *M. thermoautotrophicus* DSM3590.

The genotyping of the methanogenic microorganism to be or not to be *M. thermoautotrophicus* DSM3590 in step f) can be visually evaluated on the basis of the restriction pattern of the primer amplified product following the digestion reaction.

Thus, this at least one first restriction enzyme recognition sequence can be used in a subsequent Restriction Fragment Length Polymorphism (RFLP) analysis as widely known in the state of the art to differentiate the gained restriction pattern of the restriction enzyme treated specific amplicon of *M. thermoautotrophicus* DSM3590 from that of other non-M.-t.-DSM3590 Archaea samples, which were treated equally, especially with the at least one first restriction enzyme.

According to an embodiment of the present invention only the amplicon of the *M. thermoautotrophicus* DSM3590 results in a restriction pattern of the amplicon equal to the respective non-digested amplicon, whereas other *M. thermoautotrophicus* variants show at least two restriction fragments of specific size, most ideally of such different size to be clearly distinguished on appropriate means, especially when using gel electrophoresis owing to a single nucleotide variation in the first recognition sequence of the amplicon.

According to the present invention, first a respective region of the genomic DNA had to be found and amplified by using the primers of the present invention in order to subsequently be able to make a statement about the presence of the nucleotide sequence to be analyzed. Another prerequisite for the inventive method is the presence of a restriction enzyme recognition sequence exclusively in the *M. thermoautotrophicus* DSM3590 or on opposite in a non-*M.-thermoautotrophicus* DSM3590 (in the following "non-M.-t.-DSM3590") Archaea, owing to a single nucleotide variation.

These single nucleotide variations, also called "single nucleotide polymorphisms" (SNPs) in the amplicon were found during ongoing experimentation to be suitable to perform digestion reactions using selective restriction enzymes which recognize recognition sequences within the amplicon, wherein the presence of a recognition sequences is dependent on the identity of the respective nucleotide base of this SNP, comprised in the recognition sequence. In other words, depending on the presence and nucleotide identity of this SNP it is either recognized by the respective restriction enzyme or not, i.e., the recognition sequence is either present and readable or not present, i.e. destroyed. Therefore, the method according to the present invention allows to directly provide evidence of the presence of nucleotide variations without further sequencing of the amplicon. It can be even used to identify the respective Archaea strain owing to said single nucleotide variation.

By "single nucleotide polymorphisms (SNP)" according to the present invention is also meant any nucleotide change (transversion or transition) and even deletions or insertions of one or more nucleotides within a nucleotide sequence, which in general ultimately cause (at least) a single nucleotide change within the nucleotide sequence.

One advantage of the method, also known as PCR-RFLP or CAPS assay, underlying the method according to the present invention is to be able to easily visualize the specific fragment pattern after a digestion reaction of the PCR product by means of gel electrophoresis. It may be, e.g., in the case of a mixed Archaea culture of e.g. two Archaea variants, which differ from each other in SNP11, SNP19 or SNP20 that by applying the method according to the present invention using at least one specific restriction enzyme, which recognizes a restriction sequence, due to that SNP, wherein the SNP is located in that recognition sequence and respective different in the two different Archaea, there are specific different bands in the restriction pattern of these cultures visible in a agarose gel following gel electrophoresis. Thus, applying this method to the method according to the present invention allows to easily and advantageously distinguish M. thermoautotrophicus DSM3590 from other Archaea by simple visual means and to analyze, if there is a pure species culture or a mixed one.

Advantageously, the inventors of the present invention found that with said method it was possible to clearly identify if a given starting sample contains a pure M. thermoautotrophicus DSM3590 culture respectively comprises only M. thermoautotrophicus DSM3590 as Archaea or if it comprises also or solely non-M.-t.-DSM3590 Archaea.

Noteworthy, the present method is easy to be performed and provides reliable results to identify if in a given sample comprising methanogenic microorganisms the comprised methanogenic microorganisms only contains M. thermoautotrophicus DSM3590 or other non-M.-t.-DSM3590 methanogenic Archaea by avoiding time and cost intensive methods. Further given the present method it is possible to identify M. thermoautotrophicus DSM3590 and to differentiate it towards other methanogenic Archaea, and even to identify other M. thermoautotrophicus based strains by advantageously avoiding time and cost intensive sequencing methods, as e.g. whole genome sequencing. Given the accuracy of the inventive method even the sequencing of the amplicon generated with PCR primer pairs is not required, but of course may be performed for further quality test reasons.

Amplification of the desired region of DNA is achieved by polymerase chain reaction (PCR). By "amplification" according to the present invention is to be understood the production of additional copies of a nucleic acid sequence. This is generally carried out using PCR technologies well known in the art. "Polymerase chain reaction" or "PCR" is a method for increasing the concentration of a segment of a target sequence in a mixture of genomic DNA using PCR primers.

According to the present invention "primer" are to be understood as an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent such as DNA polymerase and at a suitable temperature and pH). The primer is preferably single stranded for maximum efficiency in amplification but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method. PCR primers are preferably at least about 10 nucleotides in length, and most preferably at least about 20 nucleotides in length. Examples of PCR primers that may be used in the methods of the invention include primers such as those found in SEQ ID NO: 1-6.

As used herein, the terms "restriction endonucleases" and "restriction enzymes" refer to bacterial enzymes, each of which cut double-stranded DNA at or near a specific nucleotide sequence known as "recognition sequence". They are "sequence specific DNA-endonucleases" capable of generating double-strand breaks in double stranded DNA in a sequence-specific manner at one or more recognition sequences. Said DNA cleavage may result in blunt ends, or so called "sticky" ends of the DNA (having a 5'- or 3'-overhang). The cleavage site may be localized within or outside the recognition sequence. Various kinds of endonucleases can be employed. Restriction enzymes are well known in the art and may be readily obtained, for example, from variety of commercial sources (for example, New England Biolabs, Inc., Beverly, Massachusetts). Similarly, methods for using restriction enzymes are also generally well known and routine in the art. Preferred restriction enzymes are those that produce at least 2 fragments of DNA when cutting the amplicon. Fragments of DNA obtained using restriction enzymes may be detected, for example, as bands by gel electrophoresis. Restriction enzymes may be used to create Restriction Fragment Length Polymorphisms (RFLPs). "RFLPs" are, in essence, unique fingerprint snapshots of a piece of DNA, whether a whole chromosome (genome), or a part thereof, such as the region of the genome comprising the SNP loci disclosed in the present invention.

RFLPs are generated by cutting ("restricting") a DNA molecule with a restriction endonuclease. Many hundreds of such enzymes have been isolated, as naturally made by bacteria. Each of the many hundreds of different restriction enzymes has been found to cut (i.e., "cleave" or "restrict") DNA at a different sequence of the 4 basic nucleotides (A, T, G, C) that make up all DNA molecules, e.g., one enzyme might specifically and only recognize the sequence A-AT-G-A-C, while another might specifically and only recognize the sequence G-T-A-C-T-A, etc. Depending on the unique enzyme involved, such recognition sequences may vary in length, from as few as 4 nucleotides to as many as 21 nucleotides. The larger the recognition sequence, the fewer restriction fragments will result, as the larger the recognition site, the lower the probability that it will repeatedly be found throughout the DNA.

Following the digestion, the resultant individual fragments are separated from one another based on their size.

Any method suitable for separating DNA is encompassed by the methods of the present invention, including, but not limited to gel electrophoresis, high performance liquid chromatography (HPLC), mass spectroscopy, and use of a microfluidic device.

In one embodiment, the DNA fragments are separated by agarose gel electrophoresis. Gel electrophoresis separates different sized charged molecules by their rate of movement through a stationary gel under the influence of an electric current. These separated DNA fragments can easily be visualized, for example, by staining with ethidium bromide and by viewing the gel under UV illumination. The banding pattern reflects the sizes of the restriction digested DNA.

Other methods that utilize the novel SNPs of the invention to detect or genotype M. thermoautotrophicus DSM3590 or to differentiate M. thermoautotrophicus DSM3590 towards variants of M. thermoautotrophicus DSM3590 are also taught herein. These methods include hybridization methods, either using a nucleic acid molecule of the invention as a probe, or a nucleic acid molecule capable of hybridizing to a disclosed nucleotide sequence of the present invention. See, for example, Sambrook et al. (1989) Molecular Cloning: Laboratory Manual (2d ed., Cold Spring Harbor Laboratory Press, Plainview, New York). Such methods using hybridization techniques are well known by a skilled person and incorporated herewith. These include, but are not limited to, techniques well known to a skilled person as Southern blotting, shift mobility assays, and Flourescent In Situ Hybridization (FISH).

In hybridization techniques, the hybridization probe(s) may be genomic DNA fragments, PCR-amplified products, or other oligonucleotides, and may comprise all or part of a known nucleotide sequence disclosed herein. In addition, it may be labeled with a detectable group such as $^{32}P$, or any other detectable marker, such as other radioisotopes, a fluorescent compound, an enzyme, or an enzyme co-factor. The term "labeled," with regard to the probe, is intended to encompass direct labeling of the probe by coupling (i.e., physically linking) a detectable substance to the probe, as well as indirect labeling of the probe by reactivity with another reagent that is directly labeled. Examples of indirect labeling include end-labeling of a DNA probe with biotin such that it can be detected with fluorescently labeled streptavidin.

Methods that encompass any hybridization technique as disclosed above may be also used to isolate the respective *M. thermoautotrophicus* DSM3590 or to isolate the respective variant.

By "sample" according to the present application is intended a liquid or solid stated source of methanogenic Archaea derived e.g. from deposited collections of microorganisms and/or alternatively obtained from a number of environmental sources, as reported in the state of the art. In general, examples of environmental sources of methanogenic microorganisms include anaerobic soils and sands, bogs, swamps, marshes, estuaries, dense algal mats, both terrestrial and marine mud and sediments, e.g. the subsurface of a tidal-flat sediment, deep ocean and deep well floors, sewage and organic waste sites and treatment facilities, and animal intestinal tracts and feces. Moreover, the "sample" comprising methanogenic Archaea can be a sample directly gained from the liquid phase of a running bioreactor, i.e. a bioprocessing fermentation.

In the understanding of the present invention, a bioreactor stands for biological reactor, and is either a bioreaction vessel, or a bioreaction enclosure, or a bioreaction tank, and/or at least a bioreaction chamber, and/or a cell, or a combination thereof, as also intended in the state of the art, able to withstand variations of e.g. temperature and/or pressure, among others, and/or able to maintain whichever imparted values of e.g. temperature, and/or pressure are assigned or have to be maintained, before, after or during the reaction process, and wherein the intended reactions relevant for carrying out the invention may take place. Such reactions are understood as bioreactions as they pertain to the domain of reactions wherein microorganisms are involved, and herein referring to their normal physiology—such as e.g. metabolic fermentation, or aerobic or anaerobic digestion—and that, as such, require suitable environments, suitable cultures of microorganisms, suitable culture mediums and suitable reactants to occur. A bioreactor in the meaning of the invention, performs reliably within the tolerance values of each variable in order to enable the method as disclosed, and it is expected to allow the listed steps to be carried out reliably over time.

In an embodiment of the present invention the method further comprises the step of:
sequencing the purified amplicon of step d. or at least parts thereof and/or the amplicon following digestion reaction of step e. or at least parts thereof. This step can be performed optional to further validate the results according to the method of the present invention as presented before.

According to an embodiment of the present invention the method further comprises the step of:
applying at least one freeze and thaw cycle to the sample containing methanogenic microorganisms according to step a. to release the DNA from the methanogenic microorganisms. Thus, it is also possible to apply means and techniques to release the DNA from the methanogenic microorganisms before a PCR reaction is performed according to step b. of said method. Other means and techniques to release the DNA from cells including single cell methanogenic microorganisms are well known to the skilled person and are encompassed herewith. To use not purified DNA generated from this approach for further PCR reactions according to the method of the present invention brings the advantage to spare a time and cost intensive purification. However, obstacles and risks for subsequent reactions may still be the fact that the amount of DNA is not calculated in non-purified DNA samples and that DNAses are present and may actively digest the genomic DNA of the sample. However, by using fresh cell samples and performing DNA preparation always on ice these factors can be controlled and minimized. Of course, it is further possible to add DNAse inhibitors to these samples, which do not interfere with components of subsequent reactions (e.g., PCR) and/or to calculate the amount of DNA using appropriated state of the art methods known by the artisan.

According to another embodiment of the method of the present invention, the method further comprises the following steps:
performing a quality control of the genotyping of step f. by performing a second digestion reaction, with the amplicon of step b. or step c. by incubating the amplicon in a reaction buffer with at least one second restriction enzyme, which recognizes a second recognition sequence, which partially overlaps with the first recognition sequence for a time sufficient to form restriction fragments;
determining the number of the formed restriction fragments and their size (restriction pattern), e.g. via gel electrophoresis and;
genotyping the methanogenic microorganism on the basis of the restriction pattern;

The second recognition sequence is at least present in the amplicon of that Archaea strain, which was not cut by the first restriction enzyme in the first digestion reaction owing to a single nucleotide polymorphism (SNP) in the second recognition sequence of the amplicon. Thus, the second recognition sequence is present in the amplicon of at least *M. thermoautotrophicus* DSM3590 or at least in the amplicon of the non-M.-t.-DSM3590 Archaea.

According to an embodiment of the present invention the second recognition sequence is present in both in the amplicon of *M. thermoautotrophicus* DSM3590 and in the amplicon of the non-M.-t.-DSM3590 Archaea.

In another embodiment the second recognition sequence is only present in the amplicon of *M. thermoautotrophicus* DSM3590 owing to a single nucleotide polymorphism (SNP) in the second recognition sequence of the amplicon and the second restriction enzyme is thus chosen on the basis to digest only the amplicon derived from *M. thermoautotrophicus* DSM3590.

Surprisingly, after identifying a restriction pattern unrelated to that of *M. thermoautotrophicus* DSM3590 the inventors have found by performing said second digestion reaction that this gives a restriction pattern useful to further distinguish said found variant from the *M. thermoautotrophicus* DSM3590.

Optionally, a genotyping step based on the amplified DNA (amplicon), e.g., measured by sequencing of the amplicon or at least parts of the amplicon of the variant can be subsequently applied, too.

This found variant related to *M. thermoautotrophicus* DSM3590 could be clearly identified and/or characterized respectively by optional genotyping said strain variant based on said amplified DNA (amplicon) and subsequent comparison with sequences found in public sequence databases to verify the genotyping of the methanogenic microorganism on the basis of the restriction pattern according to step i.) of the present inventive method. Moreover, public available programs allowing to predict the restriction sites in a given DNA sequence utilizing a specific restriction enzyme may be applied to the sequenced amplicon to advantageously further prove the observed former size dependent restriction pattern found by the inventors and thus to allow another quality control.

"Quality control" or "quality assaying" in the meaning of the present invention, refers to carefully and systematically control or verify the identity of a species/strain within the culture, in order to assess its purity. According to the present invention, purity of a species/strain means that the genome of all the individuals of said culture is comparably identical across individuals of the same mono-species/strain culture. In general, by "comparably identical" is intended nucleotide sequences of the genome that have at least 95%, 96%, 97% or 98% identity or at least 98% or 99% identity. Methods to sequence a small DNA portion as an amplicon are well known to a skilled person and include, e.g. sequencing after Sanger.

Surprisingly, according to another embodiment the inventors could even in a further step isolate said found strain variant using common methods of the state of the art. Said variant could be optionally genotyped in a further step based a comparison of the genomic DNA of that variant, e.g., evaluated by sequencing of the genomic DNA or at least parts of it.

Thus, by the present method the inventors could identify a *M. thermoautotrophicus*, denominated strain UC 120910. The strain "*Methanothermobacter thermoautotrophicus*, strain UC 120910" used in the present application is synonymously also called ECH0100 (laboratory name).

According to a further embodiment the method of the present invention is used to discriminate between the strain *M. thermoautotrophicus* DSM3590 and other *M. thermoautotrophicus* strains, or e.g. from other Archaea, the group consisting of *Methanothermobacterium, Methanobrevibacter, Methanothermobacter, Methanococcus, Methanosarcina, Methanopyrus, Methanospirillium, Methanosaeta, Methanogenium, Methanoculleus* and *Methanothermococcus* or mixtures of the aforementioned.

Sometimes cultures of Archaea may undergo natural modifications in response to the particular conditions in which the culturing has been carried out. Culture conditions are affected by several parameters, such as temperature, pH, pressure, cell density, volume, humidity, salt content, conductivity, carbon content, nitrogen content, vitamin content, amino acid content, mineral content, or a combination thereof, and according to each of these conditions a specific adaptation process may be undertaken by any number of species within the reactor environment.

The advantage of using a particular pure strain relies in the higher methanation efficiency and, therefore, in checking its identity over time to ensure that the purity is preserved. The presently provided method is highly suitable to discriminate between strains and thus to guaranty pure cultures and accordingly maintain high methanation efficiency.

According to one embodiment the provided method discriminates various strains based on at least one SNP in the amplicon, wherein this SNP is part of an overlapping sequence of the first recognition sequence of the first restriction enzyme and the second recognition sequence of the second restriction enzyme and wherein the SNP is selected from the group selected from SNP19, SNP11 and SNP20.

In the context of the present application by "SNP19" is understood as a single nucleotide polymorphism at position 418 in the PCR fragment (amplicon) of the genomic nucleotide sequence of a non-M.-t.-DSM3590 Archaea, which was PCR amplified by the primer pair SEQ ID NO: 3 (forward) and SEQ ID NO: 6 (reverse) in comparison to the PCR fragment (amplicon) of the genomic nucleotide sequence at that position of *M. thermoautotrophicus* DSM3590 amplified by the same primer pair.

In one embodiment of the present invention the non-M.-t.-DSM3590 Archaea is *M. thermoautotrophicus* UC 120910 and the single nucleotide polymorphism is a G to A transition mutation in the corresponding amplicon.

In the context of the present application by "SNP11" is intended a single nucleotide polymorphism at position 105 in the PCR fragment (amplicon) of the genomic nucleotide sequence of a non-M.t.-DSM3590 Archaea, which was PCR amplified by the primer pair, namely SEQ ID NO: 1 (forward) and SEQ ID NO: 4 (reverse) in comparison to the PCR fragment (amplicon) of the genomic nucleotide sequence at that position of *M. thermoautotrophicus* DSM3590, which was PCR amplified by the primer pair, namely SEQ ID NO: 1 (forward) and SEQ ID NO: 4 (reverse).

In the context of the present application by "SNP20" is intended a single nucleotide polymorphism at position 168 in the PCR fragment (amplicon) of the genomic nucleotide sequence of a non-M.-t.-DSM3590 Archaea, which was PCR amplified by the primer pair, namely SEQ ID NO: 2 (forward) and SEQ ID NO: 5 (reverse) in comparison to the PCR fragment (amplicon) of the genomic nucleotide sequence at that position of *M. thermoautotrophicus* DSM3590, which was PCR amplified by the primer pair, namely SEQ ID NO: 2 (forward) and SEQ ID NO: 5 (reverse).

In an embodiment of the present invention the non-M.-t.-DSM3590 Archaea identified carries as the single nucleotide polymorphism is a single base deletion mutation.

According to another embodiment the three SNPs, i.e. SNP19, SNP11 and SNP20 may be also used complementary for such a discrimination and as such the method according to the present invention may utilize SNP19, SNP11 and SNP20 in parallel for said discrimination. In the event that contradictory results are obtained and one of the results for a respective SNP differs from the other, sequencing of the amplicons in question may be performed in order to genotype the Archaea strain comprised in the sample to be analyzed.

According to another embodiment, wherein the SNP is SNP19, the first restriction enzyme is BamHI and the second restriction enzyme is AvaII. According to still another embodiment, wherein the SNP is SNP11, the first restriction enzyme is SfcI and the second restriction enzyme is BstNI or ECORII or wherein the SNP is SNP20, the first restriction enzyme is NdeI.

According to one further embodiment the non-M.-t.-DSM3590 variant identified with the method of the invention is denominated M. thermoautotrophicus UC 120910.

In a further aspect of the present invention there is provided a quality control kit for use in detecting the presence of methanogenic microorganism M. thermoautotrophicus DSM3590 within a given sample, comprising:
  at least one container
    a first primer according to claim 1 serving as forward primer;
    a second primer according to claim 1 serving as reverse primer;
    wherein the first and the second primer build up a primer pair capable to PCR amplify a DNA sequence of the methanogenic microorganism M. thermoautotrophicus DSM3590;
    at least one first restriction enzyme or at least one first and at least one second restriction enzyme according to the present invention;
    optionally at least one buffer, e.g. elution buffer, storage buffer and/or reaction buffer; and optionally
    instructions for use.

In particular, the quality control kit is intended for use in probing and genotyping a culture of methanogenic microorganisms.

The restriction enzymes as comprised in the kit are perfect to be used in RFLP analysis.

The kit may also comprise a control sample or a series of control samples (positive and negative) that can be assayed and compared to the test sample contained. Each component of the kit is usually enclosed within an individual container, and all of the various containers are within a single package along with instructions for use. The kit may also comprise a preservative or a protein-stabilizing agent.

The first and second restriction enzymes are selected from the group consisting of AvaII, Bam H I, BstNI, NdeI, SfcI and EcoRII.

Overall, the three SNP tests as provided by the kit according to the present invention may be also used complementary and as such may be performed in parallel. In the event that contradictory results are obtained and one of the assays differs from the other, sequencing of the amplicons in question should in each case be performed in order to genotype the Archaea strain comprised in the cell sample to be analyzed.

In another aspect the present invention pertains to methanogenic microorganism M. thermoautotrophicus DSM3590 variants identified by the kit according to the present invention and isolated.

In this regard, the method according the invention proofed also suitable to identify one particular variant, which is denominated M. thermoautotrophicus UC 120910.

REFERENCES

Dibrova D V, Galperin M Y, Mulkidjanian A Y. Phylogenomic reconstruction of Archaeal fatty acid metabolism. Environ Microbiol. 2014 April; 16(4):907-18. doi: 10.1111/1462-2920.12359. Environ Microbiol. 2017 January; 19(1):54-69.

Villanueva L, Schouten S, Damste J S. Phylogenomic analysis of lipid biosynthetic genes of Archaea shed light on the 'lipid divide'. Environ Microbiol. 2017 January; 19(1):54-69.

Clark C G. Riboprinting: a tool for the study of genetic diversity in microorganisms. J Eukaryot Microbiol. 1997 July-August; 44(4):277-83.

Cleland D, Krader P, Emerson D. Use of the DiversiLab repetitive sequence-based PCR system for genotyping and identification of Archaea. J Microbiol Methods. 2008 May; 73(2):172-8.

Huang, Q., Baum, L., Fu, W.-L. (2010). Simple and practical staining of DNA with GelRed in agarose gel electrophoresis. Clinical laboratory 56/3-4, 149-152.

SHORT DESCRIPTION OF THE FIGURES

FIG. 1: Agarose gel showing the results of electrophoresis of PCR products generated via temperature gradient PCR for SNP11 and SNP20 amplicon with annealing temperatures tested between 55° C. and 70° C.

Figure 2:
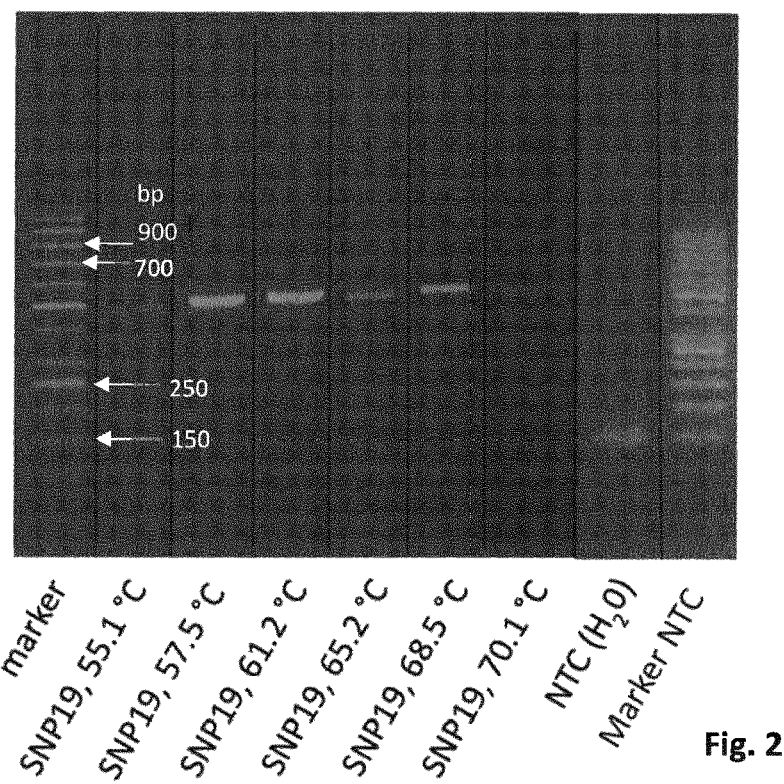

FIG. 2: Agarose gel showing the results of electrophoresis of PCR products generated via temperature gradient PCR to determine the optimal annealing temperature for SNP19 primers (lanes 9-15). From left to right side results for SNP19 amplicon were plotted with increasing annealing temperature. The negative control of the SNP19 primers was applied to a separate gel for reasons of space.

Figure 3:
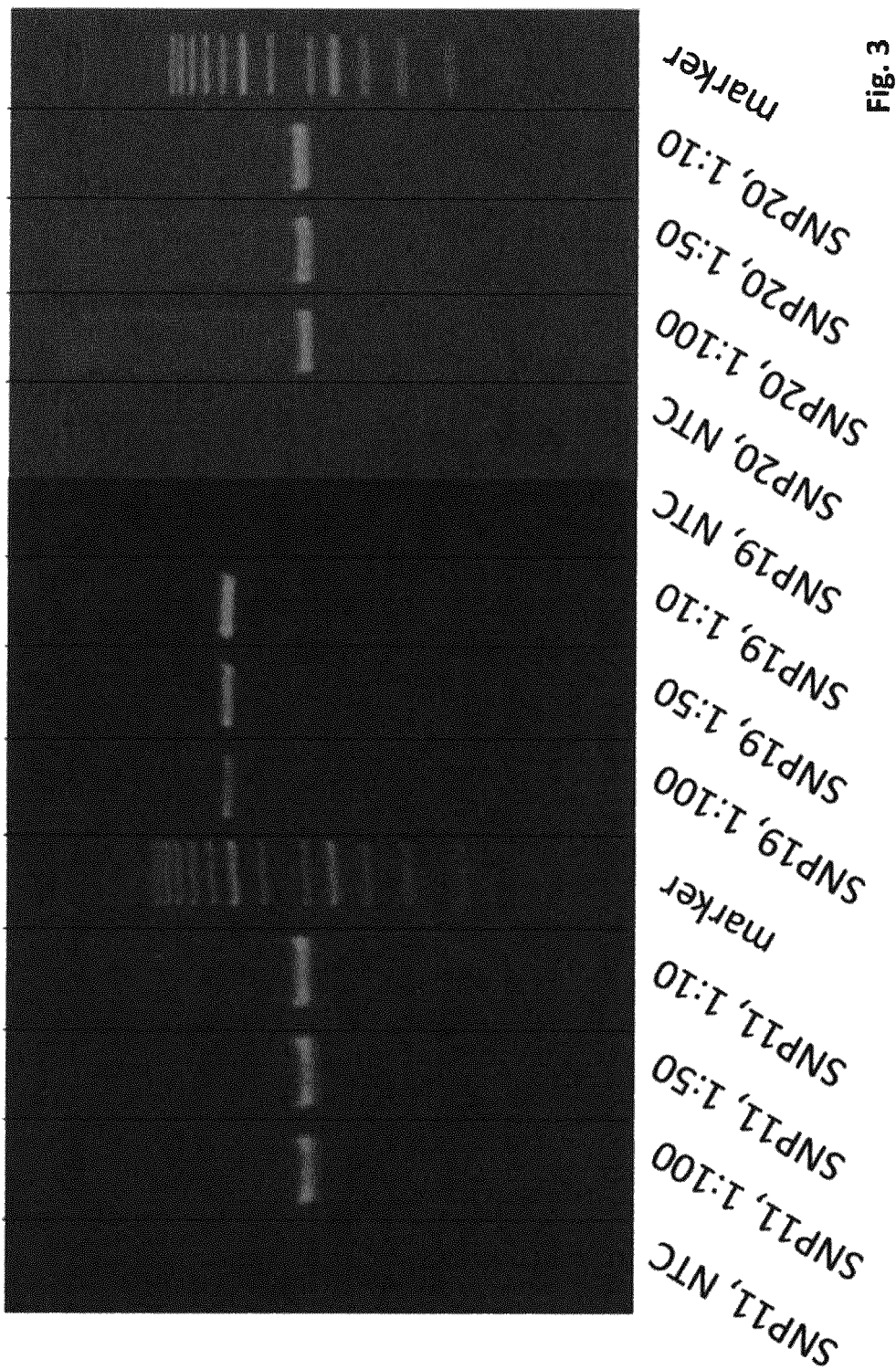

FIG. 3: Examination of Assay Sensitivity. The PCR was carried out with all primers amplifying SNP11, SNP19 and SNP20 using different dilutions (1:10, 1:50 and 1:100) of a 547 ng/µl starting DNA solution as PCR template and a respective negative control (lane "NTC").

Figure 4:
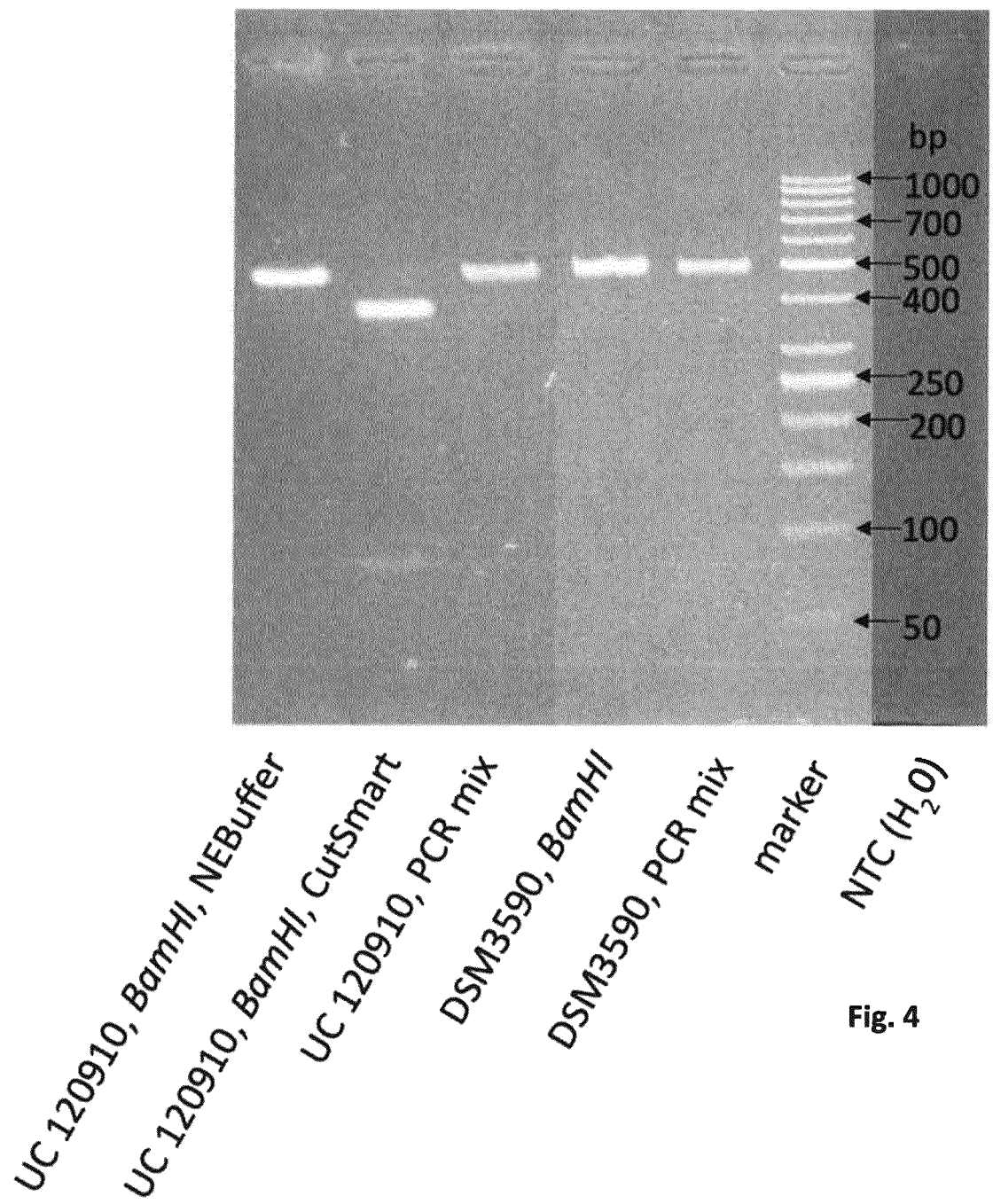

FIG. 4: Agarose gel with loaded samples from digestion reaction of SNP19 amplicon after gel electrophoresis using purified genomic DNA samples as initial templates for PCR. The amplicon of DSM3590 and the amplicon of non-M.-t.-DSM3590 Archaea were incubated with BamHI restriction enzyme for 2 h and then applied to a 2.5% agarose gel, as well as a NTC (N) and the untreated PCR amplicon. The marker (M) used was the GeneRuler 50 bp DNA Ladder from Thermo Fisher. Using NEBuffer in the digestion reaction the expected digestion reaction of the amplicon derived from non-M.-t.-DSM3590 Archaea sample did not happen and the amplicon was not cut. However, the switch from NEBuffer to CutSmart buffer resulted in the expected results. i.e. the amplicon derived from non-M.-t.-DSM3590 Archaea sample was cut and well visible on the gel.

Figure 5:
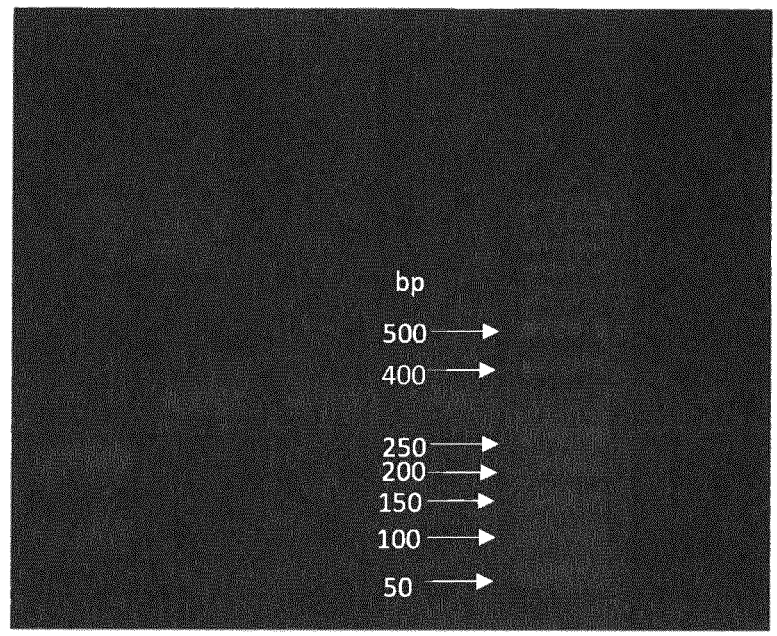

FIG. 5: Agarose gel with loaded samples from digestion reaction of SNP11 amplicon after gel electrophoresis using purified genomic DNA samples as initial templates for PCR. The amplicon of DSM3590 and the amplicon of non-M.-t.-DSM3590 Archaea were incubated with SfcI restriction enzyme for 2 h and then applied to a 2.5% agarose gel, as well as a NTC and the untreated PCR amplicon. The marker used was the GeneRuler 50 bp DNA Ladder from Thermo Fisher.

Figure 6:
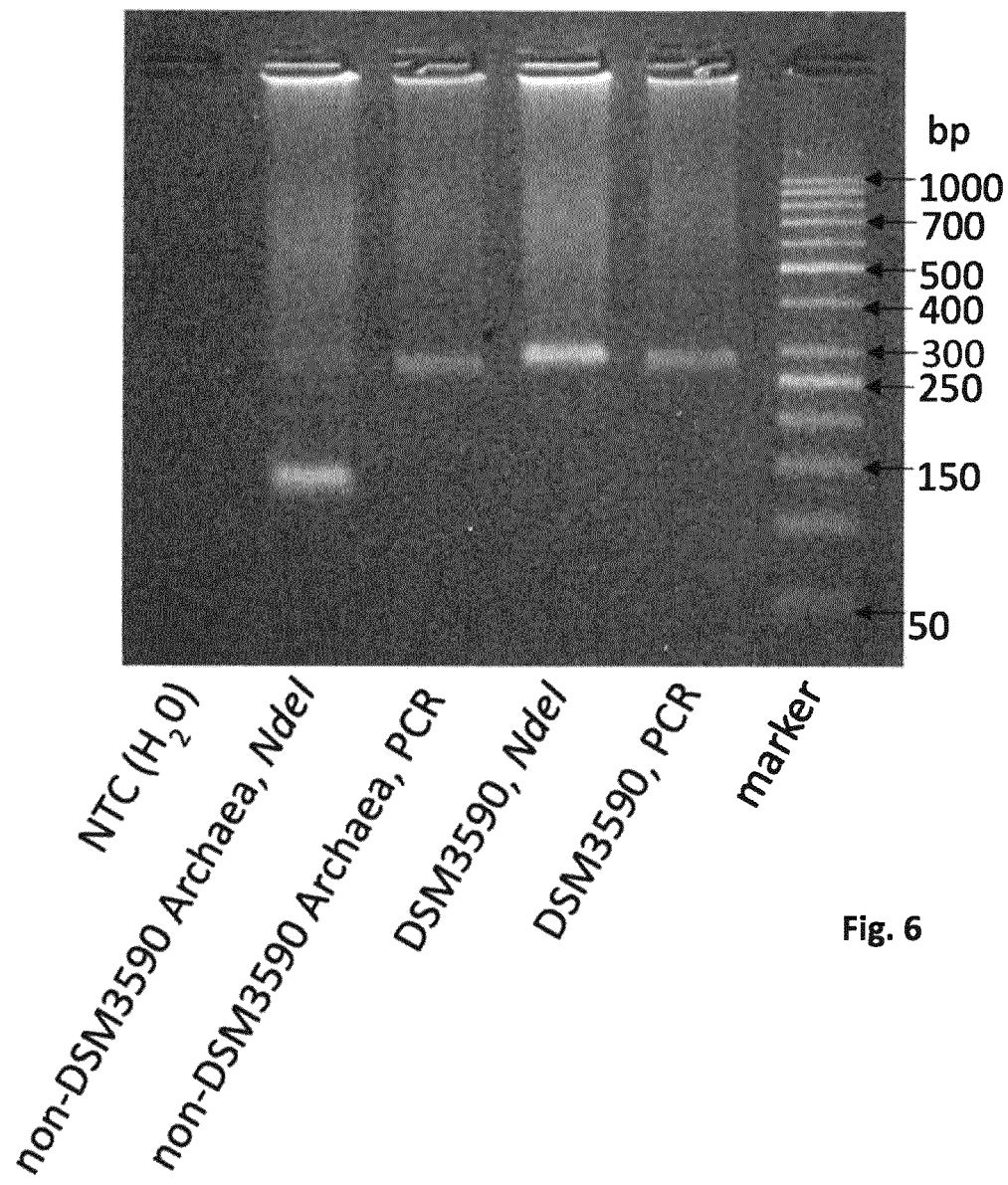

FIG. 6: Agarose gel with loaded samples from digestion reaction of SNP20 amplicon after gel electrophoresis using purified genomic DNA samples as initial templates for PCR. The amplicon of DSM3590 and the amplicon of non-M.-t.-DSM3590 Archaea were incubated with NdeI restriction enzyme in a for 2 h and then applied to a 2.5% agarose gel, as well as a NTC (N) and the untreated PCR amplicon. The marker used was the GeneRuler 50 bp DNA Ladder from Thermo Fisher.

Figure 7:
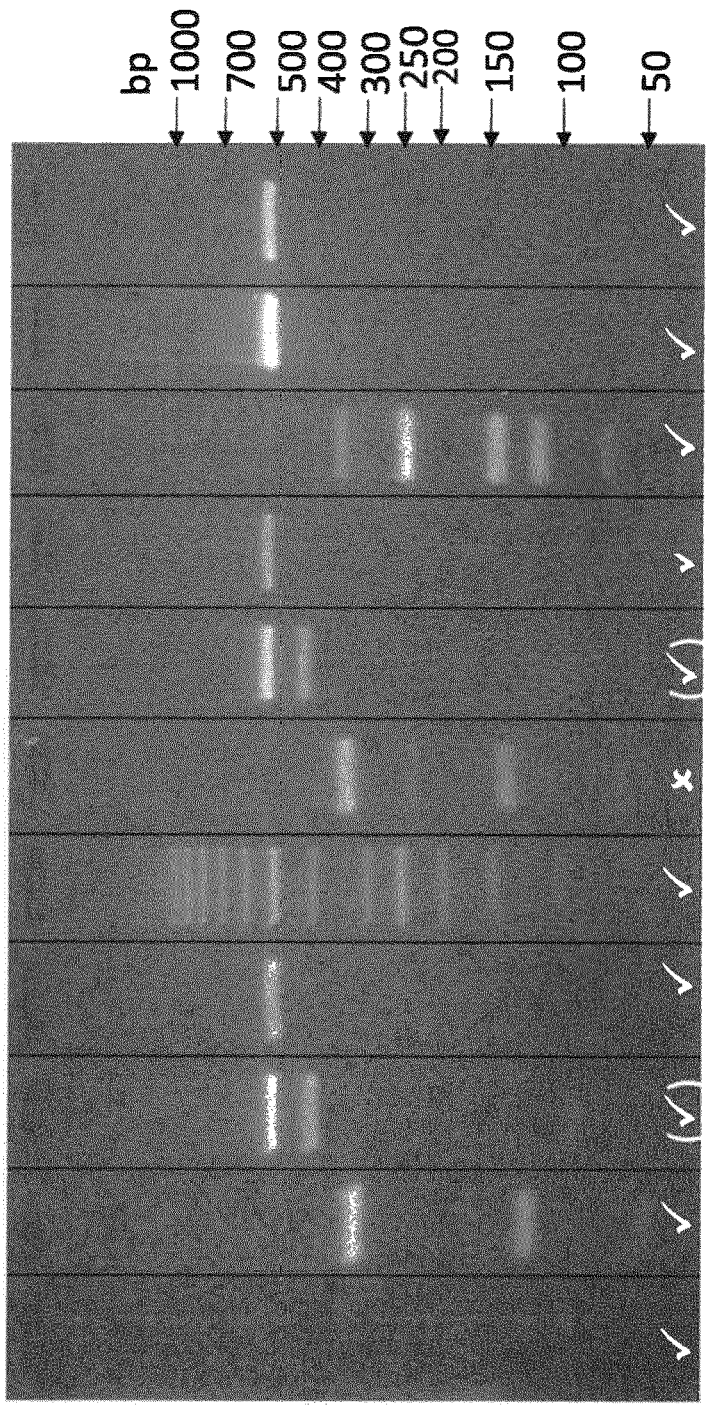

FIG. 7: Agarose gel with loaded samples from first and second digestion reactions of the SNP19 amplicon following gel electrophoresis using unpurified DNA derived from a cell sample as test template and purified DNA samples as positive controls. The UC 120910 and DSM3590 amplicon were incubated with BamHI or AvaII for 2 h each and then applied to a 2.5% agarose gel, as well as a no template control (NTC, water instead of DNA sample) and a sample of the untreated respective PCR amplicon. The molecular marker used was the GeneRuler 50 bp DNA Ladder from Thermo Fisher (✓: successful approach; (✓): successful approach; x: partially successful approach.

Figure 8:
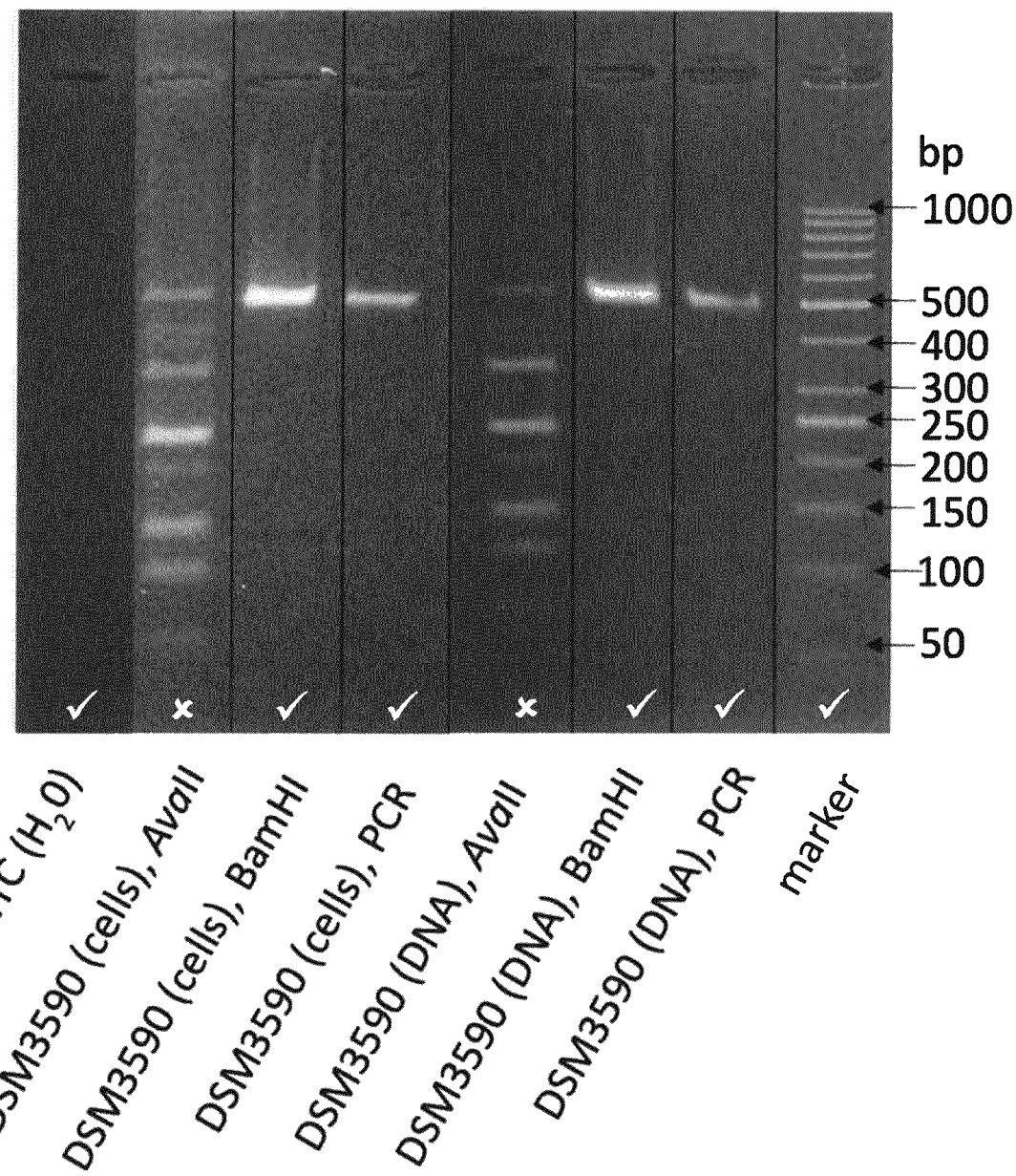

FIG. 8: Agarose gel with loaded samples from first and second digestion reactions of the SNP19 amplicon following gel electrophoresis using unpurified DNA derived from a cell sample as test template and purified DNA samples as positive controls. The UC 120910 and DSM3590 amplicon were incubated with BamHI or AvaII for 2 h each and then applied to a 2.5% agarose gel, as well as a negative control (water instead of DNA sample) and a sample of the untreated respective PCR amplicon. The molecular marker used was the GeneRuler 50 bp DNA Ladder from Thermo Fisher Specific bands were received following digestion of SNP19 amplicon with BamHI. Unspecific bands were received following digestion of SNP19 amplicon with AvaII for each of the purified DNA sample and the unpurified DNA sample derived from fresh cell preparation. ✓: successful approach; x: non-successful approach.

Figure 9:
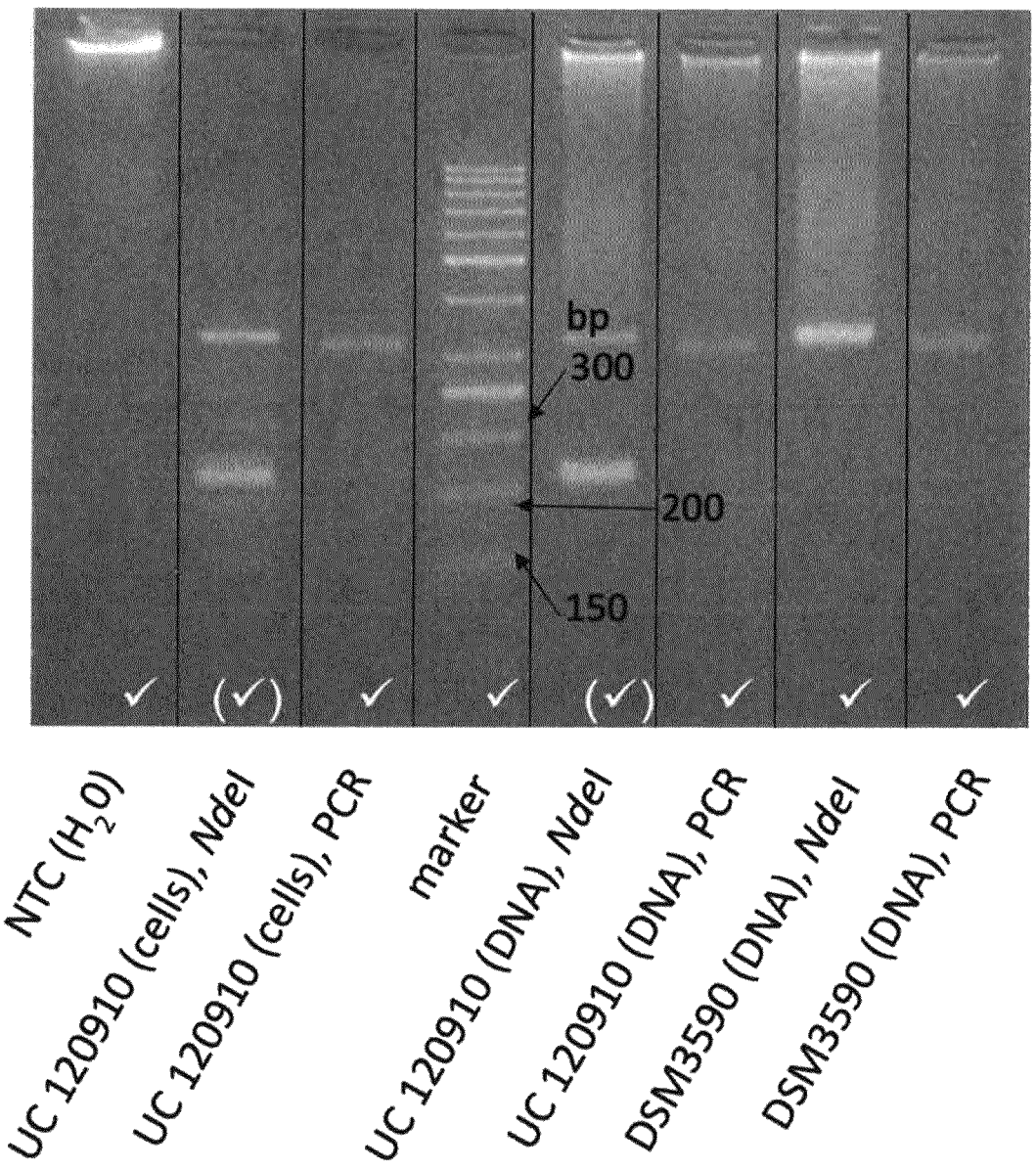

FIG. 9: Agarose gel with loaded samples from first and second digestion reactions of the SNP20 amplicon following gel electrophoresis using unpurified DNA derived from a cell sample as test template and purified DNA samples as positive controls. The UC 120910 and DSM3590 amplicon were incubated with NdeI for 2 h each and then applied to a 2.5% agarose gel, as well as a negative control (water instead of DNA sample) and a sample of the untreated respective PCR amplicon. The approach with unpurified DNA of strain UC 120910 derived from a cell sample is similar to the UC 120910 positive control: The respective amplicons were only incompletely digested. ✓: successful approach; (✓): partially successful approach.

Figure 10:
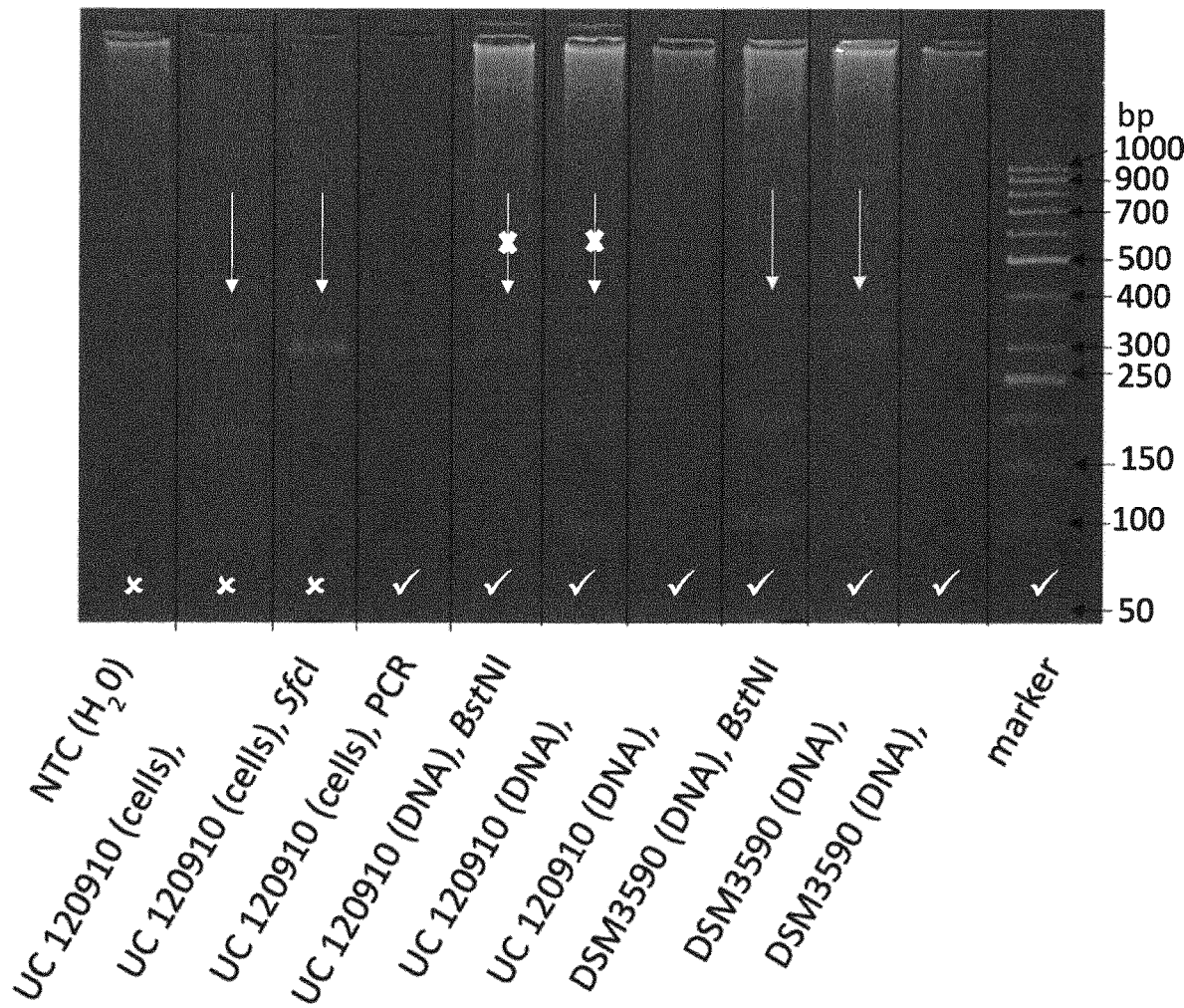

FIG. 10: Agarose gel with loaded samples from first and second digestion reactions of the SNP11 amplicon following gel electrophoresis using unpurified DNA derived from a cell sample as test template and purified DNA samples as positive controls. The UC 120910 and DSM3590 amplicon were incubated with SfcI or BstNI for 2 h each and then applied to a 2.5% agarose gel, as well as a negative control (water instead of DNA sample) and a sample of the untreated respective PCR amplicon. The molecular marker used was the GeneRuler 50 bp DNA Ladder from Thermo Fisher. Outcome: Incorrect results of the digestion reactions analysis of SNP11 using unpurified DNA samples of M. thermoautotrophicus UC 120910. The UC 120910 cell derived sample in columns 2-4 does not have the same pattern as the ECHO positive control (crossed arrows). Instead, the band pattern is similar to the positive control (arrows). ✓: successful approach; x: non-successful approach.

EXAMPLES

The following examples illustrate viable ways of carrying out the described method as intended, without the intent of limiting the invention to said examples.

General Part

The inventors of the present invention have set themselves the task to provide a simplified method for the identification of M. thermoautotrophicus DSM3590 in a given sample comprising Archaea in comparison with time consuming state of the art methods, e.g. genome sequencing and/or amplicon sequencing.

Thus, the inventors designed many primers with the purpose that these are suitable to amplify DNA sequences of M. thermoautotrophicus DSM3590 and to be suitable to distinguish from DNA sequences of other non-Methanothermobacter thermoautotrophicus Archaea and analyzed them via test and error experimentation.

Surprisingly, the inventors found that primers according to the present invention not only amplify DNA sequences of M. thermoautotrophicus DSM3590 but also amplify some other non-Methanothermobacter thermoautotrophicus Archaea. Even more interestingly the inventors found that the amplicons generated by the primers of the present invention comprised single nucleotide variations compared to other non-Methanothermobacter thermoautotrophicus Archaea, and also to other M. thermoautotrophicus DSM3590 variants. These so called SNPs in the amplicon were later found to be suitable to perform digestion reactions using selective restriction enzymes, which recognize recognition sequences within the amplicon, wherein the presence of a recognition sequences is dependent on the identity of the respective nucleotide base of this SNP, comprised in the recognition sequence. In other words, depending on the presence of a given respective nucleotide base at this SNP location it is either recognized by the respective restriction enzyme or not, i.e. the recognition sequence is either present and readable or unreadable (destroyed) for the restriction enzyme depending on the presence of the respective SNP. Therefore, the method according to the present invention allows to directly provide evidence of the presence of nucleotide variations without further sequencing of the amplicon. It can be even used to identify the respective Archaea strain owing to said single SNP base variation.

The staining in all agarose gels tested was performed using 100 fold concentrated GelRed (Biotium, Fremont, USA) using the method of Huang et al., 2010, wherein to the gel loading buffer 100 fold concentrated GelRed was added and then mixed with the respective samples and the used size marker (Gene Ruler 50 bp DNA ladder, Fisher Scientific, Schwerte, Germany).

The nucleotide sequences of the designed primers according to the present invention are indicated in Table 1.

TABLE 1

IDs (primer), Primer sequence and expected PCR generated amplicon size using genomic DNA of M. thermoautotrophicus DSM3590 as PCR template. A = adenosine; C = cytosine; G = guanine; T = thymine.

| primer name (ID) | primer sequence (5'-3') | SNP-ID | amplicon size [bp] |
|---|---|---|---|
| SEQ ID NO: 1 (forward) | TCGGCCCAGTATTTCTCATGG | SNP11 | Ca. 300 |
| SEQ ID NO: 4 (reverse) | TGGGTGGAATGGGTGGAATG | | |

TABLE 1-continued

IDs (primer), Primer sequence and expected PCR generated
amplicon size using genomic DNA of M. thermoautotrophicus
DSM3590 as PCR template. A = adenosine; C = cytosine;
G = guanine; T = thymine.

| primer name (ID) | primer sequence (5'-3') | SNP-ID | amplicon size [bp] |
|---|---|---|---|
| SEQ ID NO: 2 (forward) | TGGGTCACGTGTTCGATGAC | SNP20 | Ca. 325 |
| SEQ ID NO: 5 (reverse) | TATGAACTCCACGAGGTGCC | | |
| SEQ ID NO: 3 (forward) | CTCCACAAAGACGTCCTCCC | SNP19 | Ca. 500 |
| SEQ ID NO: 6 (reverse) | TTTAGTTGGAGGAGGATGGGG | | |

Initially, it was tried to develop a common protocol with the same experimental conditions for all PCR reactions using the inventive primer pairs, so that all assays can be carried out simultaneously. At the beginning purified genomic DNA was extracted from a pure M. thermoautotrophicus DSM3590 and a non-M.-t.-DSM3590 Archaea. The concentration of DNA of the obtained preparation was determined photometrically. As a first step, the amount of template that gave the best results for the PCR was experimentally determined. This was the case with the use of 10-20 ng of DNA, although sometimes significantly lower or higher concentrations enabled successful amplification of the templates. All primer combinations yielded fragments of the expected size (see Table 1).

The DNA polymerase used was AccuPOL polymerase. Due to its 3' to 5' exonuclease activity, it is able to screen inserted nucleotides. Proofreading activity results in an error rate of $1.1 \times 10^{-6}$ per base per duplication of amplification as reported in the state of the art. Compared to Taq DNA polymerase, the accuracy is higher. The error rate of Taq DNA polymerase is $8.0 \times 10^{-6}$ as reported in the state of the art. Based on the AccuPOL polymerase protocol, the mastermix formulation according to Table 2 is used.

TABLE 2

Master Mix for a PCR Approach.

| components | volume per reaction [µl] | Final concentration or amount |
|---|---|---|
| water | 15.48 | — |
| 10× PCR buffer[a] | 2.0 | 1× |
| dNTPs (each 12.5 mM) | 0.32 | Each 200 µM |
| forward primer (10 µM) | 0.4 | 0.2 µM |
| reverse primer (10 µM) | 0.4 | 0.2 µM |
| AccuPOL DNA polymerase (2.5 units/µl) | 57 | 1 unit |
| DNA template | 72 | ca. 50 ng |

[a]indicates: Key Buffer, VWR International, Darmstadt, Germany (comprising Tris-HCl, pH 8.8, (NH4)2SO4, 15 mM MgCl2,1% Tween 20).

To avoid the formation of experimental artifacts, the elongation time was reduced as much as possible without affecting the amplification of the longest amplicon. To minimize the total time required for amplification, the denaturation time per cycle and the initial denaturation were also shortened, resulting in significant time savings. To increase the yield and the stringency of the PCR, a temperature gradient PCR was performed for all primers. As an example, FIG. 1 shows the result for SNP11 and SNP20 and FIG. 2 shows the results for SNP19. For primers amplifying SNP11 and SNP19, the PCR with the annealing temperature 57.5° C. led to the strongest bands. Noteworthy, primers amplifying SNP19 produced only a weak band at the previous annealing temperature of 55.1° C.

The primers amplifying SNP20 worked best at the highest temperature of 70.1° C. There was a visible amount PCR product/temperature gradient. At 55.1° C. no band was visible on the gel. As the annealing temperature increased, the intensity of the bands was also increased.

The experimentally determined ideal reaction conditions were then adopted for all respective primers in the standard protocol, i.e. an annealing temperature of 57.1° C. for the primers amplifying SNP11 and SNP19 and an annealing temperature of 70.1° C. for the primers amplifying SNP20.

In order to further increase the specificity of the PCR reactions, a touchdown program was established for all assays, as far as the determined ideal annealing temperature allowed (not in case of SNP 20). This program provided for a 1° C. decrease in the annealing temperature per cycle before further amplification over several cycles at the final elongation temperature.

The applied parameters of the touchdown-PCR for the primer pairs to amplify SNP 11 (SEQ ID NO:1 (forward); SEQ ID NO:4 (reverse)) and SNP19 (SEQ ID NO:2 (forward), SEQ ID NO:5 (reverse)) are shown in Table 3.

TABLE 3

Parameters of the touchdown-PCR for the primer pairs
designed to amplify SNP11 (SEQ ID NO:1 (forward);
SEQ ID NO:4 (reverse)) and SNP19 (SEQ ID NO:2
(forward), SEQ ID NO:5 (reverse)).

| amplification steps | temperature [° C.] | duration [mm:ss] | number of PCR-cycles |
|---|---|---|---|
| Initial denaturation | 95 | 1:00 | |
| denaturation | 95 | 0:30 | |
| annealing | 70[a] | 0:30 | 14× |
| elongation | 72 | 1:00 | |
| denaturation | 95 | 0:30 | |
| annealing | 57 | 0:30 | |
| elongation | 72 | 1:00 | 16× |
| final elongation | 72 | 5:00 | |

[a]indicates that per cycle the annealing temperature is reduced by 1° C.

The primer pairs to amplify SNP 20 (SEQ ID NO:3 (forward); SEQ ID NO:6 (reverse)) have an optimal annealing temperature of 70° C. A touchdown PCR is therefore not feasible. Thus, the new annealing temperature was integrated into the improved PCR program of Table 4. The duration of each step, as well as the number of cycles has not been changed. The PCR program for amplification of SNP20 is described in Table 4.

TABLE 4

The PCR program for amplification of SNP20 using
SEQ ID NO:3 (forward); SEQ ID NO:6 (reverse).

| amplification steps | temperature [° C.] | duration [mm:ss] | number of PCR-cycles |
|---|---|---|---|
| Initial denaturation | 95 | 1:00 | |
| denaturation | 95 | 0:30 | |
| annealing | 70 | 0:30 | 30× |
| elongation | 72 | 1:00 | |
| final elongation | 72 | 5:00 | |

Using the PCR protocol now established, the sensitivity of the assays was examined by making a dilution series of the DNA template. The original concentration of the undiluted DNA template was determined photometrically and was 547 ng/µl. From this DNA solution, a 1:10, 1:50, and 1:100 dilution were made, and these solutions were each used as templates for a PCR approach with the different primer combinations (FIG. 3).

In two of the different assays (SNP11, SNP19) consistently reliable results were achieved regardless of the amount of template used. Only in the case of the SNP19 assay did the amplicon yield decrease with increasing dilution of the template. Based on these results, by default about 5 ng genomic DNA was used as template for the positive control for all further experiments, only about 50 ng template were used by default for the SNP19 PCR.

Digestion of PCR Amplicons: Testing and Optimization

All used restriction enzymes were purchased from New England BioLabs, Frankfurt am Main. Following optimization of the amplification protocol, the selected restriction enzymes were tested in a first digestion reaction to specifically not cut the amplicons generated with DNA of *M. thermoautotrophicus* DSM3590, which should remain undigested.

A series of preliminary experiments revealed that a reliable digestion reaction required purification of the PCR amplicons (data not shown). Purification of the amplicons is necessary to remove salts, primers, nucleotides and other inhibiting substances before restriction digestion. For this purpose, various purification kits were first tested (e.g. QIAquick PCR Purification Kit, Qiagen, Hilden, Germany and Roti-Prep PCR purification Kit, Carl Roth, Karlsruhe, Germany). The comparison of the kits showed that all the tested products resulted in a comparable good purified end product and therefore henceforth the kit with the lowest initial cost was used (GF-1 PCR Clean-up Kit, GeneOn, Ludwigshafen, Germany).

In a first step all of the digestion reactions were tested and optimized with amplicons prepared using purified genomic DNA as a PCR template. In a second step, the established digestion reactions were then assayed in triplicate (n=3) with amplicons generated using non-purified cell samples (see below).

Performance of the Digestion Reaction

The amplicons generated with the designed primers of the present invention were used in a first digestion reaction. Test samples were the same as above, i.e. on the one hand purified genomic DNA extracted from *M. thermoautotrophicus* DSM3590, which does not carry the recognition sequence for the applied restriction enzyme(s) within the DNA sequence to be amplified by the present specific primers and on the other hand purified genomic DNA extracted from an Archaea (non-M.-t.-DSM3590 Archaea), which does carry the recognition sequence for the applied restriction enzyme(s) within the DNA sequence to be amplified. Respective no template controls (NTC) or also called negative controls contained the respective SNP specific master mix but water ($H_2O$) instead of the DNA template.

Each amplicon template was digested with each of the amplicon-specific enzymes. Restriction was performed according to the manufacturer's instructions. According to the manufacturer (New England Biolabs), the samples can be incubated for 5-15 minutes, but also overnight, without inducing DNA degradation. An incubation period of two hours was (initially) selected. Preferably, the digestion reaction is performed in a thermocycler or in an incubator (37° C.).

Snp19

Digestion of the SNP19 PCR product with BamHI was first performed in NEBuffer 3.1 as recommended by the manufacturer, but both the *M. thermoautotrophicus* DSM3590 and the amplicon derived from non-M.-t.-DSM3590 Archaea genomic DNA remained undigested following a digestion reaction. Even when increasing the incubation times to 4 h up to an overnight incubation did not improve the result. In further tests, in addition to the NEBuffer 3.1, the CutSmart buffer (New England Biolabs, Frankfurt am Main, Germany) was used, which, according to the manufacturer, also leads to 100% activity of the enzyme. With the alternative buffer, the corresponding PCR product was hydrolyzed after only 2 h in the case of the genomic DNA of non-M.-t.-DSM3590 Archaea (see FIG. 4). Therefore, in the further experiments with the SNP19 and the restriction enzyme BamHI the CutSmart buffer was used.

SNP11

As expected in the case of the amplicon generated with the purified genomic DNA of *M. thermoautotrophicus* DSM3590 (positive control), the restriction of the amplicon did not happen and the length of the detected fragment in the agarose gel corresponded to the size of the full length PCR product initially applied in the digestion reaction. However, in the case where the sample was a specific purified non-M.-t.-DSM3590 Archaea, the genomic DNA digestion reaction of the purified SNP11 PCR product with SfcI revealed cleavage of amplicon of the non-M.-t.-DSM3590 Archaea as expected in two fragments of different length (ca. ca. 200 bp and ca. ca. 100 bp), which could be clearly visually distinguished on the applied agarose gel following gel electrophoresis (see FIG. 5).

SNP20

Similar to the digestion of the SNP11 amplicon, the digestion reaction of the SNP20 PCR product was carried out by the restriction enzyme NdeI (FIG. 6). The *M. thermoautotrophicus* DSM3590 amplicon remained undigested, i.e., was of the same size after incubation with the restriction enzyme NdeI as the untreated PCR product (ca. ca. 325 bp). However, in the case where the sample was a purified genomic DNA of a specific non-M.-t.-DSM3590 Archaea the digestion reaction of the purified SNP20 PCR product with NdeI revealed cleavage of the DNA-generated amplicon in two fragments of different length, which following gel electrophoresis could be clearly visually seen on the used agarose gel (see FIG. 6).

Testing of the Designed Primers Using Fresh Archaea Cell Samples Derived from a Running Bioreactor without a Preceding DNA Purification In a next step after the protocols for the detection reactions of the three SNPs had been established, DNA of fresh, living cells derived from a running bioreactor cell sample was used as template for the PCR amplification and prepared according to the method of the present invention. The cells of the bioreactor cell sample were only mechanically disrupted by repeated freeze (at −80° C.)—and thaw cycles, thereby releasing the DNA. The amount of released genomic DNA (unpurified DNA) was sufficient to produce comparable PCR product yields using the protocols previously developed for purified DNA (data not shown). The time consuming isolation of the genomic DNA of state of the art methods could be advantageously omitted here using the method according to the present invention. The subsequent digestion reaction of the generated amplicons was analogous to the previously examined samples. It was only to observe that the digestion reaction tended to be incomplete somewhat more frequently when using DNA from fresh cell samples of a bioreactor which was not purified before the PCR were applied than when using purified DNA for the PCR.

Assessment of Assay Reliability

Following the optimization of the test protocol, the reliability of the strain identification test was examined. For this purpose, the PCR amplification and digestion reactions of all three SNP amplicons were independently tested on three consecutive days. As a sample to be identified, Archaea cells from a running bioreactor experiment were used, which were believed to be pure *M. thermoautotrophicus* DSM3590. All primer pairs were tested under the conditions described above. Positive controls were on the one hand extracted purified DNA of *M. thermoautotrophicus* DSM3590, which does not carry the recognition sequence for the applied restriction enzymes within the DNA sequence to be amplified by the specific primers of the present invention and on the other hand specific extracted purified DNA of non-M.-t.-DSM3590 Archaea, which does carry the recognition sequence for the applied restriction enzymes within the DNA sequence to be amplified. The negative control (no template control, NTC) contained water rather than a template.

SNP19

Surprisingly, the inventors of the present invention found that the amplicon derived from Archaea cell samples, which were harvested from a running bioreactor were cut in the digestion reaction by the applied restriction enzyme BamHI at least to some extent into two fragments (see FIG. 7, lane 3), while—as expected—the amplicon derived from purified genomic DNA of *M. thermoautotrophicus* DSM3590 remained undigested (see FIG. 7, lane 10). To rule out that this was an experimental artifact, the experimentation was repeated several times even with new prepared reaction components and new prepared genomic DNA harvested from another sample of said bioreactor and even tested in a purified form (data not shown). Nevertheless, in all cases the outcome stayed comparably the same as before, i.e., following digestion reaction the amplicon was obviously cut at least to a certain extent into two distinctive sized fragments of ca. ca. 400 bp and ca. ca. 100 bp, while some of the applied amplicons sometimes remained undigested (ca. ca. 500 bp) as visible on agarose gel (see FIG. 7, lane 3). These two restriction fragments were also received following digestion reaction when using respective purified DNA samples harvested from said Archaea cell samples of the running bioreactor instead of the non-purified ones, further excluding an experimental artifact (data not shown).

To further analyze this unexpected outcome the inventors performed another parallel digesting reaction using the same amplicon samples received from the non-purified DNA approach as before for the experiment with BamHI, but instead of BamHI used another restriction enzyme, namely AvaII. This revealed a restriction pattern as can be seen on FIG. 7, lanes 2, 6 and 9. The SNP19 amplicon (ca. 500 bp) derived from the bioreactor cell sample was cut to receive three good distinguishable different sized restriction fragments (ca. 320 bp, ca. 130 bp, ca. 50 bp, see FIG. 7, lane 2). Moreover, as expected the amplicon derived from purified genomic DNA of *M. thermoautotrophicus* DSM3590 (full length ca. 500 bp) received four different sized restriction fragments (ca. 230 bp, ca. 130 bp, ca. 100 bp, ca. 50 bp; see FIG. 7, lane 9.

However, in the first round as depicted in FIG. 7, lane 6, the positive control for non-M.-t.-DSM3590 Archaea revealed weak, but specific bands in addition to the predicted bands by digesting with AvaII. This had not been observed before. In another experimentation positive control for non-M.-t.-DSM3590 Archaea was cut as expected using AvaII (data not shown), demonstrating that the results concerning that positive control of the first test run were seemingly an experimental artefact.

By subsequent amplicon sequencing it was found out that the methanogenic organism of the cell sample derived from the bioreactor is a pure culture of *M. thermoautotrophicus* UC 120910. Using a proven purified genomic DNA sample of *M. thermoautotrophicus* UC 120910 applying the method according to the present invention showed a comparable restriction pattern as compared with the cell samples of the beforementioned of *M. thermoautotrophicus* UC 120910. In more detail: The generated PCR amplicon of the purified genomic DNA sample of *M. thermoautotrophicus* UC 120910 using the SNP19 primers (see FIG. 7, lane 8) was digested using BamHI and Aval I to receive the same restriction pattern on the agarose gel as the DNA received from the aforementioned tested cell sample, which turned out to be *M. thermoautotrophicus* UC 120910, thus confirming the amplicon sequencing outcome (cf. FIG. 7, lanes 4 and 8 (PCR product); lanes 3 and 7 (BamHI digestion); lanes 2 and 9 (AvaII digestion)). The restriction efficiency for unpurified DNA samples from strain UC 120910 cell samples and UC 120910 purified DNA controls was the same in all cases, however, it could not be clarified why full digestion using BamHI for both, the non-purified DNA derived from cell samples and the purified DNA of *M. thermoautotrophicus* UC 120910 was not achieved (cf. FIG. 7, lanes 3 and 7).

In a next step the method according to the present invention was tested using a cell sample of a known *M. thermoautotrophicus* DSM3590 source. The PCR amplicon of the cell sample and the purified DNA sample was of the expected size (cf. FIG. 8, lane 14 and 17). Also, as expected was the outcome of the first digestion reaction using BamHI, which did not digest the PCR amplicon of DSM3590 at all (cf. FIG. 8, cell sample and purified DNA sample lane 13 and 16). However, unexpectedly the second digestion reaction using AvaII showed a less specific restriction pattern, i.e. more than the four expected fragments (ca. 230 bp, ca. 130 bp, ca. ca. 100 bp, ca. 50 bp) were received.

Therefore, a clear identification of the *M. thermoautotrophicus* DSM3590 could not be done on the basis of the AvaII digestion reaction. However, the results of the initial testing of the primer pair for SNP19 showed that at least with purified DNA of the *M. thermoautotrophicus* DSM3590 also the second digestion reacting using AvaII was working as expected, thus arguing that the assay is principally working.

Therefore, the method according to the present invention can be used to test for the presence of *M. thermoautotrophicus* DSM3590 and to differentiate it towards the presence of *M. thermoautotrophicus* DSM3590 variants as *M. thermo-* autotrophicus UC 120910. The received variant characteristic restriction pattern (number and size of the restriction fragments) revealed in both digestion reaction assays of the DNA derived from bioreactor cell samples of *M. thermoautotrophicus* DSM3590 and *M. thermoautotrophicus* UC 120910 can be used to genotype the methanogenic microorganism behind. Moreover, the method according to the present invention can be also further used to isolate the genotyped methanogenic microorganism behind.

The restriction efficiency for strain UC 120910 cell samples and UC 120910 purified DNA controls was the same in all cases. However, given the fact, that BamHI does not digest the DNA of *M. thermoautotrophicus* DSM3590 at all, the differentiation between the latter mentioned and *M. thermoautotrophicus* UC 120910, which shows a specific restriction pattern of at least two restriction fragments following a digesting reaction using BamHI allows to clearly differentiate between the both.

Based on the principally positive experimentation results with said cell samples from a running bioreactor containing pure *M. thermoautotrophicus* UC 120910, these were also used in the further analysis using SNP11 and SNP20 primer pairs according to the present invention. Also, the mentioned purified DNA of a proven *M. thermoautotrophicus* UC 120910 was used in any further experimentation as a positive control.

SNP11

In the first digestion reaction using the first restriction enzyme SfcI the positive controls led to the expected results in all of the runs, i.e. the amplicon was either not digested at all in the case of purified DNA of *M. thermoautotrophicus* DSM3590 or digested to result in two fragments of different and expected size in the case of purified DNA of *M. thermoautotrophicus* UC 120910. The PCR was successful in all cases, but generated weaker bands (data not shown). The analysis of the fresh cell samples from the running bioreactor, i.e. cell samples of pure *M. thermoautotrophicus* UC 120910, which should result in two fragments of different and expected size as the corresponding positive control, did not function as the amplicon of these test samples was not digested at all using the *M. thermoautotrophicus* UC 120910 specific first restriction enzyme SfcI (see FIG. 10).

In the second digestion reaction using the second restriction enzyme BstNI the positive controls led to results in all of the runs, i.e. the amplicon was either not digested at all in the case of purified DNA of *M. thermoautotrophicus* UC 120910 or digested to result in two fragments of different and expected size in the case of purified DNA of *M. thermoautotrophicus* DSM3590. The PCR was successful in all cases (data not shown).

More interestingly, the digestion of the SNP11 amplicon derived from *M. thermoautotrophicus* UC 120910 using the second restriction enzyme BstNI resulted in a DSM3590 related restriction pattern. However, BstNI should be DSM3590 specific and should not digest the amplicon of strain UC 120910 due to a SNP in the recognition sequence for that enzyme.

SNP20

Analysis of the SNP20 amplicon provided reproducible results. Restriction of the strain UC 120910 cell sample with the first restriction enzyme NdeI was successful in all cases. However, partial digestion was also partially observed in the case of the strain UC 120910 positive control and the delineation to the DSM3590 strain was clearly possible because the corresponding DSM3590 amplicon remained undigested in all cases. In more detail: The hydrolysis of the UC 120910 purified DNA (positive control) and the unpurified DNA sample derived from a fresh cell sample was in the right place in all cases: The DSM3590 control was not hydrolyzed. However, both the digestion of the unpurified DNA template and the purified DNA template were both incomplete, as shown in FIG. 9 (cf. lanes 2 and 5). However, the regular bands typical of this primer pair appeared in each run. Nevertheless, it was possible to assign the restriction pattern clearly to the UC 120910 (cf. FIG. 9).

Table 5 indicates the parameters and characteristics of the first digestion reaction and Table 6 indicates the parameters and characteristics of the second digestion reaction each for the respective SNPs and the different Archaea variant tested, i.e., *Methanothermobacter thermoautotrophicus* (M. t.) DSM3590 strain and M. t. UC 12091 strain. The used restriction enzymes as well as the number and size of the eventually generated restriction fragments following the digestion reaction are also indicated.

TABLE 5

Parameters and characteristics of the performed first digestion reaction.

| Targeted SNP | SNP11 | SNP20 | SNP19 |
|---|---|---|---|
| Amplicon size [bp] | ca. 300 | ca. 325 | ca. 500 |
| Used first restriction enzyme | SfcI | NdeI | BamHI |
| temperature used in the digestion reaction | 37° C. | 37° C. | 37° C. |
| incubation time of the digestion reaction | 2 h | 2 h | 2 h |
| first recognition sequence (5'-3') | C˜TRYAG | CA˜TA_TG | C˜GATCC |
| number of restriction fragments after digestion reaction using a pure M. t. strain UC 120910 sample | 2 | 2 | 2 |
| restriction fragment size using a pure M. t. strain UC 120910 sample | ca. 200 bp + ca. 100 bp | ca. 170 bp + ca. 160 bp | ca. 400 bp + ca. 100 bp |
| number of restriction fragments after digestion reaction using a pure M. t. strain DSM3590 sample | 1 (original amplicon) | 1 (original amplicon) | 1 (original amplicon) |
| restriction fragments after digestion reaction using a pure M. t. strain DSM3590 sample | ca. 300 bp | ca. 325 bp | ca. 500 bp |

R = A oder G (Purin); Y = C oder T (Pyrimidin); W = A oder T.

"˜" = clevage site of restriction enzyme.

"_" = frame shift.

TABLE 6

Parameters and characteristics of the performed second digestion reaction.

| Targeted SNP | SNP11 | SNP19 |
|---|---|---|
| Amplicon size [bp] | ca. 300 | ca. 500 |
| Used second restriction enzyme | BstNI | AvaII |
| temperature used in the digestion reaction | 37° C. | 37° C. |
| incubation time of the digestion reaction | 2 h | 2 h |
| second recognition sequence (5'-3') | CC˜WGG | G˜GWCC |
| number of restriction fragments after digestion reaction using a pure M. t. strain UC 120910 sample | 1 (original amplicon) | 3 |
| restriction fragment size using a pure M. t. strain UC 120910 sample | ca.300 bp | 329 bp + 133 bp + 58 bp |
| number of restriction fragments after digestion reaction using a pure M. t. strain DSM3590 sample | 2 | 4 |
| restriction fragments after digestion reaction using a pure M. t. strain DSM3590 sample | 208 + 214 | 230 bp + 133 bp + ca. 100 bp + 58 bp |

W = A oder T.
"˜" = cleavage site of restriction enzyme.
"_" = frame shift.

The results of the independent reliability tests for all four SNP PCR products (amplicons) are summarized in Table 7. The amplification of the examined genome regions from unpurified DNA derived from cell samples and genome regions from purified DNA was always successful using the established test protocol.

TABLE 7

Results of the independent reliability tests for all four SNP PCR products (amplicons).

| Amplicon | template | restriction enzyme | Expected restriction fragments [bp] | Cell sample (unpurified DNA) 1 | 2 | 3 | Purified DNA 1 | 2 | 3 |
|---|---|---|---|---|---|---|---|---|---|
| SNP11 | undigested amplicon | — | ca. 300 | ✓ | ✓ | ✓ | ✓ | ✓ | ✓ |
|  | strain UC 120910 | SfcI | ca. 200 + ca. 100 | x | x | x | ✓ | ✓ | ✓ |
|  | DSM3590 strain | SfcI | ca. 300 | — | — | — | ✓ | ✓ | ✓ |
| SNP20 | undigested amplicon | — | ca. 325 | ✓ | ✓ | ✓ | ✓ | ✓ | ✓ |
|  | strain UC 120910 | NdeI[a] | ca. 170 + ca. 160 | ✓[a] | ✓[a] | ✓[a] | ✓ | ✓[a] | ✓ |
|  | DSM3590 strain | NdeI | ca. 325 | — | — | — | ✓ | ✓ | ✓ |
| SNP19 | undigested amplicon | — | ca. 500 | ✓ | ✓ | ✓ | ✓ | ✓ | ✓ |
|  | strain UC 120910 | BamHI[a] | ca. 400 + ca. 100 | ✓ | ✓[b] | ✓ | ✓ | ✓[b] | ✓ |
|  | DSM3590 strain | BamHI | — | — | — | — | ✓ | ✓ | ✓ |

✓ = successful approach;
(✓) = partially successful approach;
x = non-successful approach;
[a] = incomplete digestion;
[b] amplicon mostly not digested.

Overall, the three SNP tests used may be considered as complementary and may be performed together in parallel. In the event that contradictory results are obtained and one of the assays differs from the other, sequencing of the amplicons in question should in each case be performed in order to genotype the Archaea strain comprised in the cell sample to be analyzed.

---

The invention claimed is:

1. A method for detecting the presence of methanogenic microorganism *Methanothermobacter thermoautotrophicus* DSM3590, comprising:
   a. obtaining a sample containing one or more methanogenic microorganisms and releasing DNA from the one or more methanogenic microorganisms to receive an unpurified DNA sample or obtaining a sample containing purified DNA of the one or more methanogenic microorganisms;
   b. using the unpurified DNA sample or the purified DNA sample according to step a in a polymerase chain reaction (PCR) amplification using a primer pair comprising a first primer and a second primer, wherein the first primer comprises a nucleotide sequence selected from the group consisting of SEQ ID NO: 1, SEQ ID NO: 2, and SEQ ID NO: 3; and the second primer comprises a nucleotide sequence selected from the group consisting of SEQ ID NO: 4; SEQ ID NO: 5, and SEQ ID NO: 6, wherein each of the first primers and each of the second primers are capable of hybridizing with the DNA of the methanogenic microorganism *Methanothermobacter thermoautotrophicus* DSM3590 and wherein the primer pair of SEQ ID NO: 1 and SEQ ID NO: 4, or SEQ ID NO: 2 and SEQ ID NO: 5, or SEQ ID NO: 3 and SEQ ID NO: 6 are used to PCR amplify said DNA, to receive an amplified DNA sequence (amplicon), wherein the amplicon comprises at least one restriction enzyme recognition sequence;
   c. purifying the amplicon;
   d. performing a first digestion reaction with the amplicon of step c by incubating the amplicon in a reaction buffer with at least one first restriction enzyme, which recognizes a first recognition sequence for a time sufficient to form restriction fragments;
   e. determining the number of the formed restriction fragments and their size (restriction pattern) and;
   f. genotyping the one or more methanogenic microorganisms on the basis of the restriction pattern.

2. The method of claim 1, further comprising:
   g. performing a quality control of the genotyping of step f by performing a second digestion reaction, with the amplicon of step b or step c by incubating the amplicon in a reaction buffer with at least one second restriction enzyme, which recognizes a second recognition sequence, which partially overlaps with the first recognition sequence for a time sufficient to form restriction fragments (digested amplicon);
   h. determining the number of the formed restriction fragments and their size (restriction pattern); and
   i. genotyping the one or more methanogenic microorganisms on the basis of the restriction pattern.

3. The method of claim 2, further comprising
   isolating a *Methanothermobacter thermoautotrophicus* DSM3590 variant; and
   optionally, genotyping the *Methanothermobacter thermoautotrophicus* DSM3590 variant.

4. The method of claim 3, wherein the method discriminates *Methanothermobacter thermoautotrophicus* DSM3590 from other *Methanothermobacter thermoautotrophicus* strains, or from other Archaea selected from the group consisting of *Methanothermobacterium, Methanobrevibacter, Methanothermobacter, Methanococcus, Methanosarcina, Methanopyrus, Methanospirillium, Methanosaeta, Methanogenium, Methanoculleus* and *Methanothermococcus* and mixtures of the aforementioned.

5. The method according to claim 4, wherein the discrimination is based on at least one SNP in the amplicon, wherein this SNP is part of an overlapping sequence of the first and the second recognition sequence and wherein the SNP is selected from the group consisting of SNP19, SNP11 and SNP20.

6. The method according to claim 5, wherein the SNP is SNP19 and wherein the first restriction enzyme is BamHI and the second restriction enzyme is AvaII, or wherein the SNP is SNP11 and the first restriction enzyme is SfcI and the second restriction enzyme is BstNI or ECORII or wherein the SNP is SNP20 and the first restriction enzyme is NdeI.

7. The method of claim 2, wherein the genotyping the one or more methanogenic microorganisms on the basis of the restriction pattern comprises detection of the presence of *Methanothermobacter thermoautotrophicus* DSM3590 based on at least one single nucleotide polymorphism (SNP) in the amplicon obtained from step b or step c,
   wherein the SNP is part of an overlapping sequence of the first and the second recognition sequence and wherein the SNP is at a position in the PCR fragment (amplicon) amplified from the genomic nucleotide sequence of *Methanothermobacter thermoautotrophicus* DSM3590 by a primer pair and compared to the same position in a PCR fragment (amplicon) of a genomic nucleotide sequence of a non-*Methanothermobacter thermoautotrophicus*-DSM3590 Archaea, which was PCR amplified by the same primer pair;
   wherein:
      a.) the position of the SNP is at position 418 (SNP19) and the primer pair is SEQ ID NO: 3 (forward) and SEQ ID NO: 6 (reverse);
      b.) the position of the SNP is at position 105 (SNP 11) and the primer pair is SEQ ID NO: 1 (forward) and SEQ ID NO: 4 (reverse); and
      c.) the position of the SNP is at position 168 (SNP 20) and the primer pair is SEQ ID NO: 2 (forward) and SEQ ID NO: 5 (reverse) and
      wherein when the SNP is SNP19, the first restriction enzyme is BamHI and the second restriction enzyme is AvaII, or when the SNP is SNP11, the first restriction enzyme is SfcI and the second restriction enzyme is BstNI or ECORII or when the SNP is SNP20, the first restriction enzyme is NdeI.

8. The method of claim 2, wherein the method discriminates *Methanothermobacter thermoautotrophicus* DSM3590 from other *Methanothermobacter thermoautotrophicus* strains, or from other Archaea selected from the group consisting of *Methanothermobacterium, Methanobrevibacter, Methanothermobacter, Methanococcus, Methanosarcina, Methanopyrus, Methanospirillium, Methanosaeta, Methanogenium, Methanoculleus* and *Methanothermococcus* and mixtures of the aforementioned.

9. The method according to claim 8, wherein the discrimination is based on at least one SNP in the amplicon, wherein this SNP is part of an overlapping sequence of the first and the second recognition sequence and wherein the SNP is selected from the group consisting of SNP19, SNP11 and SNP20.

10. The method according to claim 9, wherein the SNP is SNP19 and wherein the first restriction enzyme is BamHI and the second restriction enzyme is AvaII, or wherein the SNP is SNP11 and the first restriction enzyme is SfcI and the second restriction enzyme is BstNI or ECORII or wherein the SNP is SNP20 and the first restriction enzyme is NdeI.

11. The method of claim 1 wherein the method discriminates *Methanothermobacter thermoautotrophicus* DSM3590 from other *Methanothermobacter thermoautotrophicus* strains, or from other Archaea selected from the group consisting of *Methanothermobacterium, Methanobrevibacter, Methanothermobacter, Methanococcus, Methanosarcina, Methanopyrus, Methanospirillium, Methanosaeta, Methanogenium, Methanoculleus* and *Methanothermococcus* and mixtures of the aforementioned.

12. The method according to claim 11, wherein the discrimination is based on at least one SNP in the amplicon, wherein this SNP is part of an overlapping sequence of the first and the second recognition sequence and wherein the SNP is selected from the group consisting of SNP19, SNP11 and SNP20.

13. The method according to claim 12, wherein the SNP is SNP19 and wherein the first restriction enzyme is BamHI and the second restriction enzyme is AvaII, or wherein the SNP is SNP11 and the first restriction enzyme is SfcI and the second restriction enzyme is BstNI or ECORII or wherein the SNP is SNP20 and the first restriction enzyme is NdeI.

14. The method of claim 1, further comprising: sequencing the purified amplicon of step c or a portion thereof.

15. The method of claim 1, further comprising: sequencing the digested amplicon of step d or a portion thereof.

16. A quality control kit for use in detecting the presence of methanogenic microorganism *Methanothermobacter thermoautotrophicus* DSM3590 within a given sample, the quality control kit comprising:

at least one container;

a primer pair used to PCR amplify a DNA sequence of the methanogenic microorganism *Methanothermobacter thermoautotrophicus* DSM3590 wherein the primer pair comprises:

a first primer serving as a forward primer and comprising SEQ ID NO: 1 and a second primer serving as a reverse primer and comprising SEQ ID NO: 4, wherein at least one of the first primer and the second primer is coupled to a detectable marker selected from the group consisting of a radioisotope, a fluorescent compound, an enzyme, and an enzyme cofactor; or a first primer serving as a forward primer and comprising SEQ ID NO: 2 and a second primer serving as a reverse primer and comprising SEQ ID NO: 5, wherein at least one of the first primer and the second primer is coupled to a detectable marker selected from the group consisting of a radioisotope, a fluorescent compound, an enzyme, and an enzyme cofactor; or a first primer serving as a forward primer and comprising SEQ ID NO: 3 and a second primer serving as a reverse primer and comprising SEQ ID NO: 6, wherein at least one of the first primer and the second primer is coupled to a detectable marker selected from the group consisting of a radioisotope, a fluorescent compound, an enzyme, and an enzyme cofactor;

at least one first restriction enzyme or at least one first and at least one second restriction enzyme;

optionally at least one buffer.

* * * * *